United States Patent [19]

Howell

[11] Patent Number: 4,904,815

[45] Date of Patent: Feb. 27, 1990

[54] PHENOLS AND THEIR PRODUCTION

[75] Inventor: Frederick H. Howell, Atherton, England

[73] Assignee: Ciba-Geigy AG, Basle, Switzerland

[21] Appl. No.: 107,920

[22] Filed: Oct. 13, 1987

Related U.S. Application Data

[63] Continuation of Ser. No. 537,664, Sep. 30, 1983, abandoned.

[30] Foreign Application Priority Data

Oct. 7, 1982 [GB] United Kingdom ................ 8228643
Dec. 10, 1982 [GB] United Kingdom ................ 8235360

[51] Int. Cl.$^4$ .............................................. C07C 69/76
[52] U.S. Cl. ..................................... 560/75; 562/478; 564/170
[58] Field of Search ......................... 560/75; 562/478; 564/170

[56] References Cited

U.S. PATENT DOCUMENTS

| | | | |
|---|---|---|---|
| 3,678,095 | 7/1972 | Dexler | 560/75 |
| 3,984,460 | 10/1976 | Spivack | 562/478 |
| 3,988,363 | 10/1976 | Spivack | 562/478 |
| 3,989,738 | 11/1976 | Kline | 560/75 |
| 4,049,713 | 9/1977 | Spivack | 562/478 |
| 4,390,723 | 6/1983 | Matsuno | 562/478 |

FOREIGN PATENT DOCUMENTS

| | | | |
|---|---|---|---|
| 288465 | 3/1967 | Australia | 560/75 |
| 7135049 | 8/1982 | Japan | 562/478 |
| 203030 | 12/1982 | Japan . | |
| 1548595 | 7/1979 | United Kingdom . | |
| 2083023 | 5/1982 | United Kingdom | 562/478 |

*Primary Examiner*—Paul J. Killos
*Attorney, Agent, or Firm*—Wenderoth, Lind & Ponack

[57] ABSTRACT

New phenols are described containing an alkyl substituent containing a functional group; as well as a process for the production of such phenols. The new phenols are useful e.g. as stabilizers in organic or aqueous systems.

16 Claims, No Drawings

PHENOLS AND THEIR PRODUCTION

This application is a continuation of now abandoned application Ser. No. 537,664 filed Sept. 30, 1983.

The present invention relates to new phenols, to a process for their preparation and to their use as stabilisers and corrosion inhibitors. Phenols of similar structure are described in the Japanese patent specification No. 57203-030.

According to the present invention, there are provided compounds having the formula (I):

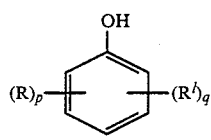

where p is 1, 2 or 3; and q is 0, 1, or 2 provided that p+q is ≦3; R is a group having the formula:

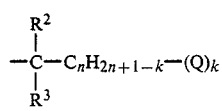

and, when p is 2 or 3, each R group may be the same or different and is present in the 2-, 4- or 6-position; n is an integer from 2 to 30; k is 1 or 2; Q is selected from the residues (i) —COOR$^4$ or —CONR$^4$R$^5$ wherein R$^4$ is H, a straight or branched chain alkyl having from 1 to 20 carbon atoms optionally interrupted by 1 to 5 oxygen atoms, and optionally substituted by a group OR$^6$ wherein R$^6$ is C$_3$–C$_{12}$ cycloalkyl, straight or branch C$_3$–C$_{20}$ alkenyl, C$_6$–C$_{10}$ aryl optionally substituted by one or two C$_1$–C$_4$ alkyl groups or C$_7$–C$_{13}$ aralkyl; divalent straight- or branched chain alkylene having 2-20 carbon atoms; a straight or branched chain alkenyl group having from 3 to 20 carbon atoms or a cycloalkyl group having from 3 to 12 carbon atoms; an aryl group having from 6 to 10 carbon atoms optionally substituted by a C$_1$–C$_4$ alkyl group; or an aralkyl group having from 7 to 13 carbon atoms; a 5- or 6-membered heterocycle containing an oxygen atom, and optionally substituted by one or two C$_1$–C$_4$ straight- or branch chain alkyl groups, or methyl substituted by a 5- or 6-membered heterocycle containing an oxygen atom and optionally substituted by one or two C$_1$–C$_4$ straight- or branch chain alkyl groups, provided that, when k is 2, the two carbon atoms to which the —COOR$^4$ groups are attached are not adjacent to one another; and R$^5$ is hydrogen or a straight or branched chain alkyl group having from 1 to 20 carbon atoms, or R$^4$ and R$^5$, together with the nitrogen atom to which they are each bonded, may from a 5- or 6-membered heterocyclic ring, optionally substituted by one or two C$_1$–C$_4$ alkyl groups;

(ii) —OX wherein X is R$^5$ or COR$^7$, wherein R$^5$ has its previous significance, R$^7$ is H or a straight- or branch chain alkyl group having from 1 to 20 carbon atoms, a straight- or branch chain alkenyl having from 3 to 20 carbon atoms, a C$_3$–C$_{12}$ cycloalkyl group, a C$_7$–C$_{13}$ aralkyl group, or a C$_6$–C$_{10}$ aryl group, optionally substituted by one or two C$_1$–C$_4$ alkyl groups;

(iii) —NR$^8$R$^9$ where R$^8$ is H or a straight- or branched chain alkyl group having 1 to 4 carbon atoms and R$^9$ is H, a straight- or branched chain alkyl group having 1 to 4 carbon atoms, or an acyl group of formula —COR$^7$ wherein R$^7$ has its previous significance, or R$^8$ and R$^9$, together with the nitrogen atom to which they are each bonded, form a 5- or 6-membered ring, optionally substituted by one or two C$_1$–C$_4$ alkyl groups;

(iv) —PO(OR$^{10}$)[O]$_x$R$^{11}$ wherein x is 0 or 1, and when x is 1, R$^{10}$ and R$^{11}$ are the same or different and each is H or a straight or branched chain alkyl group having from 1 to 20 carbon atoms; or R$^{10}$ and R$^{11}$ may be linked together to form a C$_2$–C$_3$ alkylene chain optionally substituted by one or more C$_1$–C$_{20}$ alkyl groups, and when x is 0, R$^{10}$ is H or a straight- or branched chain alkyl group having from 1 to 20 carbon atoms and R$^{11}$ is a C$_1$–C$_5$ straight chain alkyl group;

(v) CN, halogen, NO$_2$; and (vi) COR$^{12}$ where R$^{12}$ is H or a straight or branched chain alkyl group having 1 to 20 carbon atoms or halogen; R$^2$ and R$^3$ are the same or different and each is straight or branched chain alkyl group having from 1 to 5 carbon atoms and, when Q is CO$_2$R$^4$, either R$^2$ or R$^3$ is optionally substituted by a —CO$_2$R$^4$ group, the R$^4$ groups being independent, or R$^2$ or R$^3$ may be so linked to the residue C$_n$H$_{2n+1-k}$ that there is formed a C$_5$–C$_{12}$ cycloalkylene residue substituted by the group —(CO$_2$R$^4$)$_k$, the R$^4$ groups being independent, wherein R$^4$ and k have their previous significance; and, when Q is a —COR$^{12}$ group, R$^2$ or R$^3$ may be so linked to the residue C$_n$H$_{2n+1-k}$ that there is formed a C$_5$–C$_{12}$ cycloalkylene residue optionally substituted by a group —COR$^{12}$; provided that when the group Q is a CO$_2$R$_4$ residue where R$_4$ is a divalent straight or branch chain alkylene having from 1 to 20 carbon atoms, then p and k are both 1 and the compound has the formula Ia:

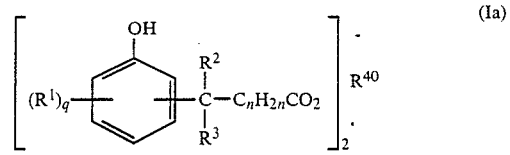

where R$^{40}$ is a divalent straight- or branch chain alkylene residue having from 2 to 20 carbon atoms; and provided that, when the group Q is a CONR$^4$R$^5$ residue where R$^4$ is a divalent straight or branch chain alkylene residue having from 2 to 20 carbon atoms, and R$^5$ has its previous significance, then p and k are both 1 and the compound of formula I has the formula Ib:

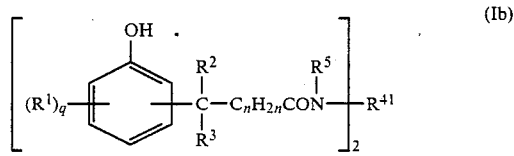

where R$^{41}$ is a divalent straight or branched chain alkyl residue having from 2 to 20 carbon atoms and R$^1$ is a C$_1$–C$_{12}$ straight- or branched chain alkyl group, a C$_7$–C$_9$ aralkyl group, halogen, CF$_3$, SH, SR$^{13}$, CO$_2$H, CO$_2$R$^{13}$, COR$^{13}$, COC$_6$H$_5$, CONH$_2$, CN, SO$_3$H, SO$_2$NH$_2$, PO(OH)$_2$, PO(OR$^{13}$)$_2$, or NO$_2$ wherein R$^{13}$ is a C$_1$–C$_4$ straight- or branched chain alkyl group, and, when q is 2, each R$^1$ group may be the same or different and when q is 1, $R^1$ in formula I can also be a residue having the formula III or IV;

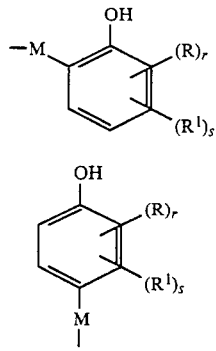

wherein R and $R^1$ have their previous significance, r is 0, 1 or 2 and s is 0 or 1, provided that $r+s \leq 2$, and M is a direct bond, $-C(R^{14})(R^{15})-$, $-S-$, $-S-S-$, $-SO-$, $-SO_2-$, $-CH_2SCH_2-$, $-O-$, $-CH_2OCH_2-$, or $-NR^{16}-$ in which $R^{14}$ and $R^{15}$ are the same or different and are hydrogen, a straight or branched chain alkyl group having 1 to 20 carbon atoms optionally interrupted by 1–3 sulphur atoms, an aryl group having 6 to 10 carbon atoms or $R^{14}$ and $R^{15}$ together with the carbon atom to which they are bonded, form a 5- or 6-membered ring which may be further substituted by one or two $C_1$–$C_8$ alkyl groups and $R^{16}$ is hydrogen, a straight or branched chain alkyl group having 1 to 12 carbon atoms, or phenyl; provided that the compound of formula I contains only one residue of formula III or IV and that this residue III or IV is present in the 2-, 4- or 6- position with respect to the OH group and provided that, when p is 1, $R^1$ is $C_1$–$C_{12}$ alkyl, $R^2$ and $R^3$ are $C_1$–$C_5$ alkyl, k is 1, Q is $-COOR^4$ wherein $R^4$ is H, and q has its previous significance, then n is not 2; and salts thereof with organic or inorganic acids and bases.

When the group $R^1$ is a $C_1$–$C_{12}$ straight- or branched chain alkyl group it may be, for example, a methyl, ethyl, n-propyl, isopropyl, n-butyl, sec-butyl, iso-butyl, t-butyl, t-amyl, 1,1,3,3-tetramethylbutyl n-decyl, or n-dodecyl group. When the group $R^2$ or $R^3$ is a $C_1$–$C_5$ straight or branched chain alkyl group it may be, for example, a methyl, ethyl, n-propyl, iso-propyl, n-butyl, sec-butyl, n-pentyl or neopentyl group.

When the group $R^4$ is a $C_1$–$C_{20}$ straight or branched chain alkyl group optionally interrupted by one to 5 oxygen atoms it may be, for example, a methyl, ethyl, 2-methoxyethyl, 2-ethoxyethyl, 2-n-propoxyethyl, 2-n-butoxyethyl, n-pentyl, n-hexyl, n-heptyl, n-octyl, 2-ethylhexyl, n-nonyl, n-decyl, n-dodecyl, n-tetradecyl, n-hexadecyl, n-octadecyl, n-eicosyl, $-(C_2H_4O)_2CH_3$, $-(C_2H_4O)_3CH_3$, $-(C_2H_4O)_4CH_3$ or $(C_2H_4O)_5CH_3$ group.

When $R^4$, $R^6$ or $R^7$ is a $C_3$–$C_{20}$ straight or branched chain alkenyl group, it may be for example, a prop-2-enyl, n-but-2-enyl, 2-methyl-prop-2-enyl, n-pent-2-enyl, n-hex-2-enyl, n-hexa-2,4-dienyl, n-dec-10-enyl, or n-eicos-2-enyl group.

When the group $R^4$, $R^6$ or $R^7$ is a $C_3$–$C_{12}$ cycloalkyl group, it may be, for example, a cyclopropyl, cyclobutyl, cyclopentyl, cyclohexyl, cyclooctyl, cyclodecyl, adamantyl, or cyclododecyl group. When the group $R^4$, $R^6$ or $R^7$ is a $C_7$–$C_{13}$ aralkyl group it may be, for example, a benzyl, phenylethyl, benzhydryl, or naphthylmethyl group.

When the group $R^4$, $R^6$ or $R^7$ is a $C_6$–$C_{10}$ aryl group optionally substituted by a $C_1$–$C_4$ straight or branched chain alkyl group, it may be, a phenyl, tolyl, xylyl, cumyl, butylphenyl or naphthyl group.

When the group Q is a $-COOR^4$ group and $R^4$ is a 5- or 6-membered heterocycle containing oxygen, and optionally substituted by one or two straight- or branch chain $C_1$–$C_4$ alkyl groups, it may be, for example, tetrahydrofuran-3-yl, tetrahydropyran-4-yl or 2,6-dimethyl-tetrahydropyran-4-yl. When the group $R^4$ is methyl substituted by a 5- or 6- membered heterocycle containing an oxygen atom, and optionally substituted by one or two straight- or branch chain $C_1$–$C_4$ alkyl groups, it may be, for example, furfuryl, tetrahydrofurfuryl or tetrahydropyran-2-yl.

When the group $R^8$, $R^9$ and $R^{13}$ is a $C_1$–$C_4$ straight or branched chain alkyl group it may be for example, a methyl, ethyl, n-propyl, iso-propyl, n-butyl or sec-butyl group.

When the groups $R^4$ and $R^5$ and the groups $R^8$ and $R^9$, together with the nitrogen atom to which they are bonded, form a 5- or 6- membered heterocyclic ring, optionally substituted by one or two $C_1$–$C_4$ alkyl groups, this ring may be a pyrrolidine, piperidine, morpholine or a 2,5-dimethyl morpholine ring.

When the groups $R^5, R^7, R^{10}, R^{11}, R^{12}, R^{14}, R^{15}$ and $R^{16}$ are $C_1$–$C_{20}$ straight or branched chain alkyl they may be the same or different and may be methyl, ethyl, n-propyl, isopropyl, n-butyl, sec-butyl, n-pentyl, n-hexyl, n-heptyl, n-octyl, 2-ethylhexyl, n-nonyl, n-decyl, n-dodecyl, n-tetradecyl, n-hexadecyl, n-octadecyl or n-eicosyl groups.

When the groups $R^{10}$ and $R^{11}$ are linked to form a $C_2$ or $C_3$ methylene chain optionally substituted by one or more $C_1$–$C_{20}$ alkyl chains, they may be for example $-CH_2CH_2-, CH_2-CH_2-CH_2-$, $-CH_2CH(CH_3)-$, $-CH_2CH(C_2H_5)-$, $-CH_2CH(C_{20}H_{41})-$, $-CH(CH_3)CH(CH_3)-$, $-CH-(CH_3)C(CH_3)_2-$, $-C(CH_3)_2C(CH_3)_2-$, $-CH_2CH_2-C(CH_3)_2-$, or $CH(CH_3)CH_2CH(CH_3)-$ groups.

When the groups $R^{14}$ and $R^{15}$, together with the carbon atom ring to which they are bonded, form an optionally substituted $C_5-$ or $C_6-$ring, this ring may be a cyclopentane, cyclohexane, 4-t-butyl cyclohexane or 2,6-dimethyl cyclohexane ring.

When the group $R^{40}$ or $R^{41}$ is a divalent straight or branched chain alkylene group having from 2 to 20 carbon atoms it may be, for example, $-CH_2CH_2-$, $-(CH_2)_3-$, $-(CH_2)_4-$, $-(CH_2)_5$, $-(CH_2)_{14}-$, $-(CH_2)_{16}-$, $-(CH_2)_{18}-$, $-(CH_2)_{20}-$. $-CH_2CH(CH_3)-$, $-CH_2C(CH_3)_2-$, $-CHCH_3CHCH_3-$, or $-C(CH_3)_2C(CH_3)_2-$.

When the group Q and $R^1$ is halogen it may be fluorine, chlorine, bromine or iodine. When the group $R^{12}$ is halogen it may be chlorine or bromine.

Examples of salts include salts with alkali and alkaline earth metals and amines and, where Q is a $NR^8R^9$ group, salts with organic and inorganic acids for example, hydrochloric, sulphuric, para-toluene-sulphonic and oxalic acids.

In one preferred embodiment, the compounds of the invention have the formula (V):

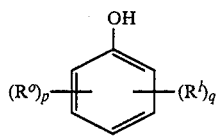

wherein $R^1$, p and q have their previous significance and $R^0$ is a residue of formula:

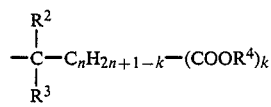

or

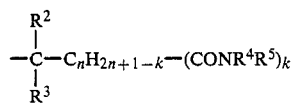

in which n, k, $R^2$, $R^3$, $R^4$ and $R^5$ have their previous significance.

More preferred compounds of formula V are those where k=1; particularly preferred are those where $R^0$ is a residue of formula IIa; especially preferred are those wherein $R^2$ and $R^3$=$CH_3$ and $R^1$ is a $C_1$-$C_5$ straight or branch chain alkyl; and most especially preferred are those where n=3.

Other preferred compounds of the invention are those having the formula I wherein p is 1 and q, n, k, $R^1$, $R^2$ $R^3$ and Q have their previous significance. More preferred compounds of this embodiment are those where k=1; particularly preferred are those where $R^2$ and $R^3$=$CH_3$ and $R^1$ is a $C_1$-$C_5$ straight or branch chain alkyl; and most particularly preferred are those where n=3 to 10.

In particular, those compounds of formula V are preferred which do not contain a residue of formula III or IV.

Non-limiting examples of compounds of formula I include:

5-(2-Hydroxyphenyl)-5-methyl-hexanoic acid and its sodium salt
5-(4-Hydroxyphenyl)-5-methyl-hexanoic acid and its sodium salt
Methyl 5-(2-hydroxyphenyl)-5-methyl-hexanoate
Methyl 5-(4-hydroxyphenyl)-5-methyl-hexanoate
n-Hexyl 5-(4-hydroxyphenyl)-5-methyl-hexanoate
2-Ethylhexyl 5-(4-hydroxyphenyl)-5-methyl-hexanoate
Eicosyl 5-(4-hydroxyphenyl)-5-methyl-hexanoate
2-Butoxyethyl 5-(4-hydroxyphenyl)-5methyl-hexanoate
2-Cyclohexyloxyethyl 5-(4-hydroxyphenyl)-5-methyl-hexanoate
2-Allyloxyethyl 5-(4-hydroxyphenyl)-5-methyl-hexanoate
2-Phenoxyethyl 5-(4-hydroxyphenyl)-5-methyl-hexanoate
2-(4-Methylphenoxy)-ethyl 5-(4-hydroxyphenyl)-5-methyl-hexanoate
2-Benzyloxyethyl 5-(4-hydroxyphenyl)-5-methyl-hexanoate
Allyl 5-(4-hydroxyphenyl)-5-methyl-hexanoate
Undecenyl 5-(4-hydroxyphenyl)-5-methyl-hexanoate
Cyclohexyl 5-(4-hydroxyphenyl)-5-methyl-hexanoate
Phenyl 5-(4-hydroxyphenyl)-5-methyl-hexanoate
4-Methylphenyl 5-(4-hydroxyphenyl)-5-methyl-hexanoate
Benzyl 5-(4-hydroxyphenyl)-5-methyl-hexanoate
Tetrahydrofurfuryl 5-(4-hydroxyphenyl)-5-methyl-hexanoate
Furfuryl 5-(4-hydroxyphenyl)-5-methyl-hexanoate
Tetrahydropyran-4-yl 5-(4-hydroxyphenyl)-5-methyl-hexanoate
5-(4-hydroxyphenyl)-5-methylhexanoic acid amide
N-Methyl-5-(4-hydroxyphenyl)-5-methylhexanoic acid amide
N-n-Butyl-5-(4-hydroxyphenyl)-5-methylhexanoic acid amide
N,N-Dimethyl-5-(4-hydroxyphenyl)-5-methylhexanoic acid amide
N,N-Diethyl-5-(4-hydroxyphenyl)-5-methylhexanoic acid amide
N,N-Di-n-butyl-5-(4-hydroxyphenyl)-5-methylhexanoic acid amide
N,n-Eicosyl-5-(4-hydroxyphenyl)-5-methylhexanoic acid amide
N-Allyl-5-(4-hydroxyphenyl)-5-methylhexanoic acid amide
N-Cyclohexyl-5-(4-hydroxyphenyl)-5-methylhexanoic acid amide
N-Benzyl-5-(4-hydroxyphenyl)-5-methylhexanoic acid amide
N-Phenyl-5-(4-hydroxyphenyl)-5-methylhexanoic acid amide
N-[5-(4-Hydroxyphenyl)-5-methyl-hexanoyl]-morpholine
Methyl 5-(4-hydroxy-3-methylphenyl)-5-methyl-hexanoate
Allyl 5-(4-hydroxy-3-methylphenyl)-5-methyl-hexanoate
Cyclohexyl 5-(4-hydroxy-3-methylphenyl)-5-methyl-hexanoate
Methyl 5-(2-hydroxy-5-methylphenyl)-5-methyl-hexanoate
5-(2-Hydroxy-5-methylphenyl)-5-methyl-hexanoic acid
5-(2-Hydroxy-3,5-di-methylphenyl)-5-methyl-hexanoic acid
Methyl 5-(2-hydroxy-3,5-di-methylphenyl)-5-methyl-hexanoate
Methyl 5-(4-hydroxy-3,5-di-methylphenyl)-5-methyl-hexanoate
5-(5-Ethyl-2-hydroxyphenyl)-5-methyl-hexanoic acid
Methyl 5-(5-ethyl-2-hydroxyphenyl)-5-methyl-hexanoate
Methyl 5-(3-ethyl-4-hydroxyphenyl)-5-methyl-hexanoate
Methyl 5-(3,5-di-ethyl-4-hydroxyphenyl)-5-methyl-hexanoate
Methyl 5-(5-n-decyl-2-hydroxyphenyl)-5-methyl-hexanoate
5-(2-Hydroxy-5-isopropylphenyl)-5-methyl-hexanoic acid
Methyl 5-(2-hydroxy-5-isopropylphenyl)-5-methyl-hexanoate
Methyl 5-(4-hydroxy-3-isopropylphenyl)-5-methyl-hexanoate
Methyl 5-(2-hydroxy-3,5-di-isopropylphenyl)-5-methyl-hexanoate
Methyl 5-(4-hydroxy-3,5-di-isopropylphenyl)-5-methyl-hexanoate
Methyl 5-(3-sec-butyl-4-hydroxyphenyl)-5-methyl-hexanoate Methyl 5-(3-t-butyl-2-hydroxy-5-methylphenyl)-5-methyl-hexanoate
Methyl 5-(3-t-butyl-4-hydroxy-5-methylphenyl)-5-methyl-hexanoate
Methyl 5-(3-cumyl-4-hydroxy-phenyl)-5-methyl-hexanoate
Methyl 5-(3-cumyl-4-hydroxy-5-methyl-phenyl)-5-methyl-hexanoate
Methyl 5-(3-t-butyl-2-hydroxy-5-isopropylphenyl)-5-methyl hexanoate
Methyl 5-(3,5-di-t-butyl-2-hydroxyphenyl)-5-methyl-hexanoate
Methyl 5-(3,5-di-t-butyl-4-hydroxyphenyl)-5-methyl-hexanoate
Methyl 5-[2-hydroxy-5-(1,1,3,3-tetramethylbutyl)-phenyl]-5-methyl-hexanoate
5-(3-t-Butyl-2-hydroxy-5-methylphenyl)-5-methyl-hexanoic acid
5-(3-t-Butyl-2-hydroxy-5-methylphenyl)-5-methyl-hexanoic acid chloride
Bis-[5-(3-t-butyl-4-hydroxy-5-methylphenyl)-5-methyl-hexanoate]ester of 1,6-hexanediol
Bis-[5-(3-t-butyl-4-hydroxy-5-isopropylphenyl)-5-methyl-hexanoate]ester of 1,6-hexanediol
Bis-[5-(3,5-di-t-butyl-4-hydroxyphenyl)-5-methyl-hexanoate]ester of 1,6-hexanediol
5-(3-t-Butyl-2-hydroxy-5-methyl-phenyl)-5-methyl-hexanoic acid amide of 1,1,3,3-tetramethylbutylamine
5-(3-t-Butyl-2-hydroxy-5-methyl-phenyl)-5-methyl-hexanoic acid amide of n-dodecylamine
Bis-5-(3-t-butyl-2-hydroxy-5-methyl-phenyl)-5-methyl-hexanoic acid amide of 1,6-diamino-hexane
Methyl 5-(5-chloro-2-hydroxyphenyl)-5-methyl-hexanoate
Methyl 5-(3-chloro-2-hydroxyphenyl)-5-methyl-hexanoate
Methyl 5-(3-chloro-4-hydroxyphenyl)-5-methyl-hexanoate
Methyl 5-(3,5-dichloro-4-hydroxyphenyl)-5-methyl-hexanoate
2,4-Bis-(5-methoxycarbonyl-2-methyl-pent-2-yl)-phenol
2,6-Bis-(5-methoxycarbonyl-2-methyl-pent-2-yl)-phenol
2,6-Bis-(5-methoxycarbonyl-2-methyl-pent-2-yl)-4-methyl-phenol
2,4,6-Tris-(5-carboxy-2-methyl-pent-2-yl)-phenol
2,4,6-Tris-(5-methoxycarbonyl-2-methyl-pent-2-yl)-phenol
2,4-Bis-(5-carboxy-2-methyl-pent-2-yl)-phenol
2,6-Bis-(5-carboxy-2-methyl-pent-2-yl)-4-methyl-phenol
2-(8-n-Butyloxy-2,6-dimethyl-oct-2-yl)-4-(5-methoxycarbonyl-2-methyl-pent-2-yl)-phenol
2,6-Bis-(5-carboxy-2-methyl-pent-2-yl)-phenol
4-(7-Methoxycarbonyl-2,2,4-trimethyl-hept-4-yl)-phenol
Methyl 5-(4-hydroxyphenyl)-2-methoxycarbonyl-5-methyl-hexanoate
2-Carboxy-5-(2-hydroxy-5-methylphenyl)-5-methyl-hexanoic acid
Methyl 5-(2-hydroxy-5-methylphenyl)-2-methoxy-carbonyl-5-methyl-hexanoate
Dimethyl 5-methyl-5-(2-hydroxyphenyl)-azelate
Dimethyl 5-methyl-5-(4-hydroxyphenyl)-azelate
7-(4-Hydroxyphenyl)-3,7-dimethyl-octan-1-ol
7-(2-Hydroxy-5-methylphenyl)-3,7-dimethyl-octan-1-ol
1-n-Butyloxy-7-(4-hydroxy-3,5-dimethyl-phenyl)-3,7-dimethyl-octane
1-Acetoxy-7-(4-hydroxyphenyl)-3,7-dimethyl-octane
1-Eicosoyloxy-7-(4-hydroxyphenyl)-3,7-dimethyl-octane
1-Crotonyloxy-7-(4-hydroxyphenyl)-3,7-dimethyl-octane
1-Cyclohexancarbonyloxy-7-(4-hydroxyphenyl)-3,7-dimethyl-octane
1-Phenylacetoxy-7-(4-hydroxyphenyl)-3,7-dimethyl-octane
1-Benzoyloxy-7-(4-hydroxyphenyl)-3,7-dimethyl-octane
1-(4-Methylbenzoyloxy)-7-(4-hydroxyphenyl)-3,7-dimethyl-octane
6-(2-Hydroxyphenyl)-6-methyl-2-methylamino-heptane
6-(2-Hydroxyphenyl)-6-methyl-2-dimethylamino-heptane
2-n-Ethylamino-6-(4hydroxyphenyl)-6-methyl-heptane
2-n-Butylamino-6-(2-hydroxyphenyl)-6-methyl-heptane
2-di-n-Butylamino-6-(2-hydroxyphenyl)-6-methyl-heptane
6-(2-Hydroxyphenyl)-6-methyl-2-morpholino-heptane
2-Amino-6-(2-hydroxyphenyl)-6-methyl-heptane and its hydrochloride salt
2-Amino-6-(4-hydroxyphenyl)-6-methyl-heptane and its hydrochloride salt
2-Acetamido-6-(2-hydroxyphenyl)-6-methyl-heptane
2-Acetamido-6-(4-hydroxyphenyl)-6-methyl-heptane
2-Eicosamido-6-(4-hydroxyphenyl)-6-methyl-heptane
2-Crotonamido-6-(4-hydroxyphenyl)-6-methyl-heptane
2-Cyclohexancarbonamido-6-(4-hydroxyphenyl)-6-methyl-heptane
2-Benzamido-6-(4-hydroxyphenyl)-6-methyl-heptane
Dimethyl 3-(2-hydroxyphenyl)-3-methyl-butane-phosphonate
Dimethyl 3-(4-hydroxyphenyl)-3-methyl-butane-phosphonate
Diethyl 3-(4-hydroxyphenyl)-3-methyl-butane-phosphonate
Dimethyl 3-(2-hydroxy-5-methylphenyl)-3-methyl-butane-phosphonate
Dimethyl 3-(4-hydroxy-3,5-dimethylphenyl)-3-methyl-butane-phosphonate
Dimethyl 3-(4-hydroxy-3,5-di-isopropylphenyl)-3-methyl-butane-phosphonate
Diethyl 7-(4-hydroxyphenyl)-3,7-dimethyl-octane-phosphonate
Diethyl 2-ethoxycarbonyl-5-(2-hydroxyphenyl)-5-methyl-hexane phosphonate
Diethyl 2-ethoxycarbonyl-5-(4-hydroxyphenyl)-5-methyl-hexane phosphonate
3-(2-Hydroxyphenyl)-3-methyl-butane-phosphonic acid
3-(2-Hydroxy-5-methylphenyl)-3-methyl-butane-phosphonic acid
3-(2-Hydroxyphenyl)-3-methyl-butane-methylphosphonic acid and its sodium acid
Di-dodecyl 3-(4-hydroxyphenyl)-3-methyl-butyl-phosphonate
2-[3-(4-Hydroxyphenyl)-3-methyl-butyl]-2-oxo-1,3,2-dioxaphospholane
1-Bromo-7-(4-hydroxyphenyl)-3,7-dimethyl-octane
7-(2-Hydroxyphenyl)-3,7-dimethyl-1-nitro-octane
7-(4-Hydroxyphenyl)-3,7-dimethyl-1-nitro-octane
1-Acetoxy-3-(4-hydroxyphenyl)-3-methyl-butane
6-(2-Hydroxyphenyl)-6-methyl-heptan-2-one
6-(4-Hydroxyphenyl)-6-methyl-heptan-2-one
cis-[4-Acetyl-1-(4-hydroxyphenyl)]-1-methyl-cyclohexane
trans-[4-Acetyl-1-(4-hydroxyphenyl)]-1-methyl-cyclohexane 1-Cyano-4-(2-hydroxyphenyl)-4-methyl-pentane
1-Cyano-4-(4-hydroxyphenyl)-4-methyl-pentane
cis-[4-Cyano-1-(4-hydroxyphenyl)]-1-methyl-cyclohexane
trans-[4-Cyano-1-(4-hydroxyphenyl)]-1-methyl-cyclohexane
Ethyl 2-cyano-5-(4-hydroxyphenyl)-5-methyl-hexanoate
cis-[1-(4-Hydroxyphenyl)-4-methoxycarbonyl]-1-methyl-cyclohexane
trans-[1-(4-Hydroxyphenyl)-4-methoxycarbonyl]-1-methyl-cyclohexane
cis-[1-(2-Hydroxyphenyl)-4-methoxycarbonyl]-1-methyl-cyclohexane
trans-[1-(2-Hydroxyphenyl)-4-methoxycarbonyl]-1-methyl-cyclohexane
cis-[1-(4-Hydroxyphenyl)-cis-3,4-di-methoxycarbonyl]-1-methyl-cyclohexane
trans-[1-(4-Hydroxyphenyl)-cis-3,4-di-methoxycarbonyl]-1-methyl-cyclohexane
cis-[1-(2-Hydroxy-5-methylphenyl)-4-methoxycarbonyl]-1-methyl-cyclohexane
trans-[1-(2-Hydroxy-5-methylphenyl)-4-methoxycarbonyl]-1-methyl-cyclohexane
cis-[1-(4-Hydroxy-3,5-di-isopropylphenyl)-4-methoxycarbonyl]-1-methyl-cyclohexane
trans-[1-(4-Hydroxy-3,5-di-isopropylphenyl)-4-methoxycarbonyl]-1-methyl-cyclohexane
trans-[1-(4-Hydroxy-3,5-di-isopropylphenyl)-4-carboxy]-1-methyl-cyclohexane
trans-[1-(3,5-di-t-Butyl-4-hydroxyphenyl)-4-methoxycarbonyl]-1-methyl-cyclohexane
Bis-[4-methyl-trans-(4-(3,5-di-t-butyl-4-hydroxyphenyl)-cyclohexane-1-carboxylic acid)] ester of hexane-1,6-diol
5-(5-Carboxy-2-methyl-pent-2-yl)-2-hydroxybenzoic acid
Methyl 2-hydroxy-5-(5-methoxycarbonyl-2-methyl-pent-2-yl)-benzoate
3,5-Bis-(5-carboxy-2-methyl-pent-2-yl)-2-hydroxy-benzoic acid
Methyl 2-hydroxy-3,5-bis-(5-methoxycarbonyl-2-methyl-pent-2-yl)-benzoate
5-(6-Amino-2-methyl-hept-2-yl)-2-hydroxy-benzoic acid
Methyl 5-(6-amino-2-methyl-hept-2-yl)-2-hydroxy-benzoate
2-Hydroxy-5-(2-methyl-4-phosphono-but-2-yl)-benzoic acid
Methyl 2-hydroxy-5-(2-methyl-4-dimethylphosphono-but-2-yl)-benzoate
Methyl 4-hydroxy-3-(5-methoxycarbonyl-2-methyl-pent-2-yl)-benzoate
2-Hydroxy-5-(5-methoxycarbonyl-2-methyl-pent-2-yl)-acetophenone
2-Hydroxy-3-(5-methoxycarbonyl-2-methyl-pent-2-yl)-acetophenone
4-Hydroxy-3-(5-methoxycarbonyl-2-methyl-pent-2-yl)-acetophenone
2-Hydroxy-5-(5-methoxycarbonyl-2-methyl-pent-2-yl)-benzophenone
2-Hydroxy-3-(5-methoxycarbonyl-2-methyl-pent-2-yl)-benzophenone
4-Hydroxy-3-(5-methoxycarbonyl-2-methyl-pent-2-yl)-benzophenone
2-Cyano-4-(5-methoxycarbonyl-2-methyl-pent-2-yl)-phenol
4-Cyano-2-(5-methoxycarbonyl-2-methyl-pent-2-yl)-phenol
2-Hydroxy-5-(5-methoxycarbonyl-2-methyl-pent-2-yl)-benzoamide
4-Hydroxy-3-(5-methoxycarbonyl-2-methyl-pent-2-yl)-benzamide
4-(5-Methoxycarbonyl-2-methyl-pent-2-yl)-2-methyl-mercapto-phenol
2-(5-Methoxycarbonyl-2-methyl-pent-2-yl)-4-methyl-mercapto-phenol
4-(5-Methoxycarbonyl-2-methyl-pent-2-yl)-2-trifluoromethyl-phenol
2-Hydroxy-5-(5-methoxycarbonyl-2-methyl-pent-2-yl)-benzene-sulphonic acid
2-Hydroxy-5-(5-methoxycarbonyl)-2-methyl-pent-2-yl)-benzene-sulphonamide
2-Hydroxy-5-(5-methoxycarbonyl-2-methyl-pent-2-yl)-benzene-phosphonic acid
Diethyl 2-hydroxy-5-(5-methoxycarbonyl-2-methyl-pent-2-yl)-phenylphosphonate
4-(5-Methoxycarbonyl-2-methyl-pent-2-yl)-2-nitro-phenol
Bis-[2-hydroxy-5-(5-methoxycarbonyl-2-methyl-pent-2-yl)-3-methyl-phenyl]-methane
Bis-[2-hydroxy-3-(5-methoxycarbonyl-2-methyl-pent-2-yl)-5-methyl-phenyl]-methane
Bis-[4-hydroxy-5-(5-methoxycarbonyl-2-methyl-pent-2-yl)-3-methyl-phenyl]-methane
Bis-2,2-[4-hydroxy-5-(5-methoxycarbonyl-2-methyl-pent-2-yl)-3-methyl-phenyl]-propane
Bis-1,1-[2-hydroxy-5-(5-methoxycarbonyl-2-methyl-pent-2-yl)-3-methyl-phenyl]-cyclohexane
Bis-[2-hydroxy-5-(5-methoxycarbonyl-2-methyl-pent-2-yl)-3-methyl-phenyl]-sulphide
Bis-[2-hydroxy-5-(5-methoxycarbonyl-2-methyl-pent-2-yl)-3-methyl-phenyl]-disulphide
Bis-[2-hydroxy-3-(5-methoxycarbonyl-2-methyl-pent-2-yl)-5-methyl-phenyl]-sulphoxide
Bis-[2-hydroxy-5-(5-methoxycarbonyl-2-methyl-pent-2-yl)-3-methyl-phenyl]-sulphone
Bis-[2-hydroxy-3-(5-methoxycarbonyl-2-methyl-pent-2-yl)-3-methyl-benzyl]-sulphide
Bis-[4-hydroxy-5-(5-methoxycarbonyl-2-methyl-pent-2-yl)-3-methyl-phenyl]-oxide
Bis-[2-hydroxy-5-(5-methoxycarbonyl-2-methyl-pent-2-yl)-3-methyl-benzyl]-oxide
4,4-Dihydroxy-5,5'-(5-methoxycarbonyl-2-methyl-pent-2-yl)-3,3'-dimethyl-diphenylamine The present invention provides a process for the production of compounds of formula I comprising reacting, in the presence of a suitable catalyst, a phenol having the formula

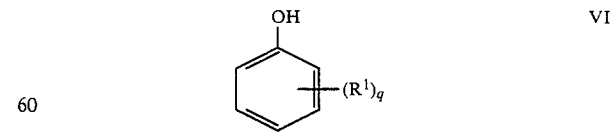

wherein $R^1$ has its previous significance and q is 0, 1 or 2, provided that the compound of formula VI contains only one residue of formula III or IV bonded in the 2-, 4- or 6-position relative to the OH group, with a functional alkylating agent VII capable of introducing a group of formula:

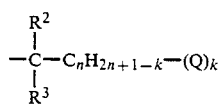

$$-\underset{R^3}{\overset{R^2}{\underset{|}{\overset{|}{C}}}}-C_nH_{2n+1-k}-(Q)_k \quad \text{(II)}$$

wherein $R^2$, $R^3$, Q, n and k have their previous significance. The alkylation step is conveniently carried out at a temperature ranging from 20° to 170° preferably 100°–150°. The catalyst may be a Brönsted acid, an active earth, or a metal salt. Brönsted acids suitable for the purpose may be organic or inorganic or a partial salt thereof and may be an inorganic mineral acid such as hydrochloric, sulphuric, perchloric, and orthophosphoric acid; an alkyl, aryl, or alkaryl substituted inorganic acid such as methane and ethane sulphonic acids, benzene sulphonic acid, p-toluene sulphonic acid and methane phosphonic acid; an organic acid such as dichloro acetic acid, trichloroacetic acid, and trifluoroacetic acids. Active earths suitable for alkylation include Fulmont 237 ® and Fulcat 22 ®, while aluminium phenoxide is a suitable metal salt.

Preferred catalysts are the active earths.

The reaction may be carried out with or without a solvent, convenient solvents include hydrocarbons such as benzene, cyclohexane, heptane. Other solvents include methanol/sulphuric acid or water/sulphuric acid and the solvent here acts as a catalyst. Compounds of formula I may be obtained from compounds of formula VI by reaction with from 0.1 to 4.0 moles of alkylating agent VII per mole of compound of formula VI. More particularly, when it is required for compounds of formula I that p is 1, q being 0, 1 or 2, then 0.1 to 1.0 moles of alkylating agent VII per mole of compound of formula VI are used; when p is 2, q being 0 or 1, then at least 2 moles of alkylating agent VII per mole of compound of formula VI are used; and when $R^1$ is a residue of formula III or IV in which s is 0 or 1 and r is 0 or 1, then up to 4 moles of alkylation agent VII are used per mole of compound VI.

Alternatively, compounds of formula I in which p is 2 or 3 and for which the R groups II may be the same or different, these may be prepared by introducing sequentially into compounds of formula I for which p is 1 or 2, the R group II, using at least 1 mole of VII per mole of I.

Alternatively, compounds of formula I where p is 1 or 2, q is 1 or 2 and $R^1$ is a $C_4$–$C_8$ alkyl group may be prepared from compounds of formula I where q is 0 or 1 and p is 1 or 2 by alkylation of I with at least one mole of a $C_4$–$C_8$ olefin or alcohol in the presence of an acid catalyst.

Compounds of formula I containing a residue of formula III or IV, as hereinbefore defined, may be produced by methods well-known per se, e.g., by condensing 2 moles of a compound of formula I in which q is 0 and p is 1 or 2 with an agent capable of introducing the linkage M.

Examples of Phenols VI include
Phenol
o-Cresol
m-Cresol
p-Cresol
2,6-Xylenol
2,4-Xylenol
2-Ethylphenol
4-Ethylphenol
2,6-Diethylphenol
2-iso-Propylphenol
4-iso-Propylphenol
2,6-di-iso-Propylphenol
2-sec-Butylphenol
4-sec-Butylphenol
2,6-di-sec-Butylphenol
4-t-Butyl-phenol
4-(1,1,3,3-Tetramethylbutyl)-phenol
4-n-Decylphenol
2-Chlorophenol
4-Chlorophenol
2,6-Dichlorophenol
2-Chloro-4-methyl-phenol
Salicylic acid
Methyl salicylate
4-Hydroxybenzoic acid
Methyl p-hydroxy-benzoate
2-Hydroxyacetophenone
2-Hydroxybutyrophenone
4-Hydroxyacetophenone
2-Hydroxybenzophenone
4-Hydroxybenzophenone
2-Cyanophenol
4-Cyanophenol
2-Hydroxybenzamide
4-Hydroxybenzamide
2-Methylmercaptophenol
4-Methylmercaptophenol
4-n-Butylmercaptophenol
2-Trifluromethylphenol
4-Trifluoromethylphenol
2-Hydroxybenzenesulphonic acid
4-Hydroxybenzenesulphonic acid
2-Hydroxybenzenesulphonamide
4-Hydroxybenzenesulphonamide
2-Hydroxybenzenephosphonic acid
4-Hydroxybenzenephosphonic acid
Diethyl 2-hydroxyphenylphosphonate
Diethyl 4-hydroxyphenylphosphonate
2-Nitrophenol
4-Nitrophenol
4,4'-Dihydroxydiphenylmethane
4,4'-Dihydroxy-3,3'-dimethyl-diphenylmethane
2,2-(4,4'-Dihydroxydiphenyl)-propane
1,1-(4,4'-Dihydroxydiphenyl)-cyclohexane
4,4'-Dihydroxydiphenylamine
4,4'-Dihydroxydiphenylether Functional alkylating agents VII which are reacted with the phenol VI contain a reactive centre, for example, an olefinic or hydroxy group which is eliminated, transformed or rearranged during the course of the alkylation reaction. Examples of functional olefins suitable for the functional alkylation of compounds of formula VI are:
5-Methyl-hex-5-enoic acid
Methyl 5-methyl-hex-4-enoate
Methyl 5-methyl-hex-5-enoate
Ethyl 5-methyl-hex-5-enoate
n-Hexyl 5-methyl-hex-5-enoate
2-Ethylhexyl 5-methyl-hex-5-enoate
n-Hexadecyl 5-methyl-hex-5-enoate
Methyl 5,7,7,-trimethyl-oct-4-enoate
1,7-Dimethoxycarbonyl-4-methyl-hept-3-ene
1-Acetoxy-3-methyl-but-3-ene
Citronellol
Citronellyl acetate
Citronellyl n-butylether Citronellic acid
Methyl citronellate
Citronellyl nitrile
1-Bromo-3,7-dimethyl-oct-6-ene
3,7-Dimethyl-1-nitro-oct-6-ene
Diethyl 3,7-dimethyl-oct-6-ene-1-phosphonate
Methyl 2-methoxycarbonyl-5-methyl-hex-4-enoate
Ethyl 2-ethoxycarbonyl-5-methyl-hex-4-enoate
Diethyl 2-ethoxycarbonyl-5-methyl-hex-4-ene-2-phosphonate
Ethyl 2-cyano-5-methyl-hex-4-enoate
Dimethyl prenyl phosphonate
Diethyl prenyl phosphonate
1-Cyano-4-methyl-pent-4-ene
6-Methyl-hept-6-en-2-one
2-Amino-6-methyl-hept-5-ene and hydrochloride
2-Amino-6-methyl-hept-6-ene and hydrochloride
2-Acetamido-6-methyl-hept-5-ene
2-Acetamido-6-methyl-hept-6-ene
4-Methoxycarbonyl-1-methyl-cyclohex-1-ene
4-Cyano-1-methyl-cyclohex-1-ene
4-Acetyl-1-methyl-cyclohex-1-ene Examples of functional hydroxy compounds suitable for functional alkylation of compounds of formula VI are:

2-Amino-6-hydroxy-6-methyl-heptane and hydrochloride
2-Acetamido-2-hydroxy-6-methyl-heptane
11-Amino-2,2,12-trimethyl-tridecan-1-ol as well as members selected from 11-amino-undecanols of the formula:

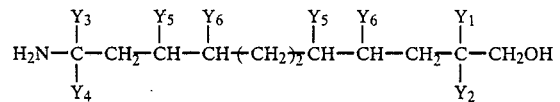

wherein $Y_1$ and $Y_3$, independently, are H or $C_1$-$C_8$ alkyl; $Y_2$ and $Y_4$, independently, are $C_1$-$C_8$ alkyl; and $Y_5$ and $Y_6$, independently, are H or $C_1$-$C_4$ alkyl.

These 11-amino-undecanols are described in more detail, together with their method of manufacture in German Offenlegungsschrift No. 2831299. Examples of olefins suitable for the alkylation of compounds of formula I wherein q is 0 or 1 and p is 1 or 2 are isobutylene and diisobutylene. Examples of alcohols suitable for the alkylation of compounds of formula I wherein q is 0 or 1 and p is 1 or 2 are t-butanol and 1,1,3,3-tetramethylbutan-1-ol. Any functional derivative of a compound of formula I may be converted to a different functional derivative. For example when Q is the acid group $CO_2H$ it may be esterified with a monovalent alcohol $R^4OH$ to give the corresponding ester $CO_2R^4$, with a divalent alcohol $R^{40}(OH)_2$ to give the corresponding ester $-CO_2)_2R^{40}$, or when Q is the ester group $CO_2R^4$ it may be transesterified to give a different $R^4$ or $R^{40}$ group or alternatively the ester group $-CO_2R^4$ may be converted to an amide $CONR^4R^5$ by treatment with an amine $NHR^4R^5$ wherein $R^4$ and $R^5$ have their previous significance or with a diamine $R^5HN$-$R^{41}$-$NHR^5$ wherein $R^5$ is independently as previously described. The compounds of formula 1 are useful as stabilisers and anti-oxidants for example for polymer, oil or photographic systems, and as corrosion inhibitors. The compounds of formula 1 are also useful as intermediates for photographic chemicals.

Accordingly, the present invention also provides a composition comprising a substrate and, as stabiliser, a compound of formula I, as previously defined.

In one preferred embodiment, the substrate is an aqueous medium in contact with metals, especially ferrous metals, and the compound of formula I functions to inhibit corrosion of the metal by the aqueous medium.

In a further preferred embodiment, the substrate system is an organic material susceptible to oxidative decomposition e.g. a polymeric material, an oil or a photographic system and the compound of formula I functions as an antioxidant, optionally as a thermal antioxidant.

The following Examples further illustrate the present invention. Parts and percentages shown therein are by weight; pressures are in millibars.

EXAMPLE 1

(a) 94 Parts of phenol, 14.2 parts of methyl 5-methyl-hex-5-enoate, and 5.0 parts of Fulmont 237® were stirred at 110° C. for 20 hours. The partly cooled reaction mixture was then filtered free of catalyst and distilled. After recovering 82 parts of phenol there was obtained methyl 5-(4-hydroxyphenyl)-5-methyl-hexanoate $b_{0.85}167°$-72° C. with the following percentage composition by weight.

| | Carbon | Hydrogen |
|---|---|---|
| Found | 71.01 | 8.60 |
| Calculated for $C_4H_{20}O_3$ | 71.16 | 8.53 |

(b) 5.0 Parts of methyl 5-(4-hydroxyphenyl)-5-methyl-hexanoate from Example 1a, 5.0 parts of sodium hydroxide, and 50 parts of water were refluxed for 3 hours. The homogeneous solution after acidification with 36% hydrochloric acid gave an oil which solidified on cooling. The solid was filtered off and recrystallised from 40°-60° C. petroleum-ether at 0° C. to give 5-(4-hydroxyphenyl)-5-methyl-hexanoic acid m.p. 94°-6° C. with the following percentage composition by weight.

| | Carbon | Hydrogen |
|---|---|---|
| Found | 70.33 | 8.22 |
| Calculated for $C_{13}H_{18}O_3$ | 70.24 | 8.16 |

EXAMPLE 2

94 Parts of phenol, 28.5 parts of 4-methoxycarbonyl-1-methylcyclohex-1-ene, and 5.0 parts of Fulmont 237® were reacted and worked up as in Example 1. The fraction $b_{0.4}167°$-94° C. consisting of the cis and trans isomers of 1-(4-hydroxyphenyl)-4-methoxycarbonyl-1-methyl-cyclohexane was fractionally crystallised from ether. The initial crop of crystals gave after crystallisation from methanol and water the trans-isomer m.p. 120°-2° C. with the following percentage composition by weight.

| | Carbon | Hydrogen |
|---|---|---|
| Found | 72.59 | 8.03 |
| Calculated for $C_{15}H_{20}O_3$ | 72.55 | 8.12 |

The ethereal mother liquors which provided the first crop of crystals were concentrated to yield a further crop of crystals, and these after crystallisation from methanol and water gave the cis-isomer m.p. 128°–30° C. with the following percentage composition by weight.

|  | Carbon | Hydrogen |
|---|---|---|
| Found | 72.01 | 7.91 |
| Calculated for $C_{15}H_{20}O_3$ | 72.55 | 8.12 |

Examples 3 to 20 in the following table further exemplify esters prepared according to the procedure described in Example 1.

| EXAMPLE | Phenol (parts) | Alkylating Agent (parts) | Catalyst (parts) | Reaction Temp. °C. | Reaction Time hours | Products | bp/pressure °C./mb | m.p. °C. | Molecular Formula | Found & required % composition Carbon | Hydrogen | Chlorine |
|---|---|---|---|---|---|---|---|---|---|---|---|---|
| 3 | OH-C₆H₅ (94) | 4-methylcyclohex-3-enyl-CO₂CH₃ (30.8) | Al(OPh)₃ from Al (0.3) | 175 | 40 | 2-(4-methylcyclohexyl)phenol-CO₂CH₃ isomers | 190–250/13 | | C₁₅H₂₀O₃ | 72.80 / 72.55 | 8.12 / 8.12 | |
| 4 | OH-C₆H₅ (94) | cyclohexene with two CO₂CH₃ and CH₃ (21.2) | Fulmont 237 ® (5.0) | 110 | 18 | 4-substituted phenol dimethyl ester isomers | 196–200/0.5 | 125–7, 129–31 | C₁₇H₂₂O₅ | 66.65 / 66.65 | 7.36 / 7.24 | |
| 5 | OH-C₆H₅ (94) | branched chain with CO₂CH₃ (39.6) | Fulmont 237 ® | 140 | 48 | 4-alkylphenol CO₂CH₃ | 152–62/0.3 | | C₁₈H₂₈O₃ | 73.66 / 73.93 | 9.35 / 9.65 | |
| 6 | OH-C₆H₅ (14.1) | branched chain diester CO₂CH₃, CO₂CH₃ (84) | Fulmont 237 ® (10) | 130 | 18 | 4-alkylphenol diester | 200/0.13 wiped wall still | | C₁₆H₂₂O₅ | 65.37 / 65.29 | 7.89 / 7.53 | |
| 7 | OH-C₆H₅ (94) | methylcyclohexene diester CO₂CH₃, CO₂CH₃ (45.6) | Fulmont 237 ® (5.0) | 140 | 20 | 2-substituted phenol with diester | 210–6/0.13 | | | | | |

-continued

| EXAMPLE | Phenol (parts) | Alkylating Agent (parts) | Catalyst (parts) | Reaction Temp. °C. | Reaction Time hours | Products | bp/pressure °C./mb | m.p. °C. | Molecular Formula | Found & required % composition Carbon | Hydrogen | Chlorine |
|---|---|---|---|---|---|---|---|---|---|---|---|---|
| 8 | OH (phenol) (37.8) | ⟋⟍CO₂CH₃ (28.4) | Fulmont 237 ® (5.0) | 125 | 20 | HO-C₆H₄-C(CH₂CO₂CH₃)(CH₂CO₂CH₃) type structure | | | $C_{18}H_{26}O_5$ | 67.05 / 67.08 | 8.26 / 8.07 | |
| 9 | o-cresol (108) | ⟋⟍CO₂CH₃ (56.8) | Fulmont 237 ® (5.0) | 125 | 20 | substituted phenol with CO₂CH₃ groups; →KOH→ CO₂H analog | 200-10/ 0.3 | 61-3 | $C_{22}H_{34}O_5$ | 70.03 / 69.81 | 8.80 / 9.05 | |
| | | | | | | (after KOH hydrolysis product) | | 132-4 | $C_{20}H_{30}O_5$ | 68.88 / 68.55 | 8.61 / 8.63 | |
| 10 | p-cresol (108) | ⟋⟍CO₂CH₃ (56.8) | Fulmont 237 ® (5.0) | 150 | 24 | methyl-substituted phenol with CH(CH₃)CO₂CH₃ group; →NaOH→ CO₂H analog | 152-69/ 0.3 | 56-7 | $C_{15}H_{22}O_3$ | 72.21 / 71.97 | 8.87 / 8.86 | |
| | | | | | | | 144-6/1.3 | | $C_{15}H_{22}O_3$ | 72.03 / 71.97 | 8.74 / 8.86 | |
| | | | | | | | | 101-3 | $C_{14}H_{20}O_3$ | 71.08 / 71.16 | 8.67 / 8.53 | |

| EXAMPLE | Phenol (parts) | Alkylating Agent (parts) | Catalyst (parts) | Reaction Temp. °C. | Reaction Time hours | Products | bp/pressure °C./mb | m.p. °C. | Molecular Formula | Found & required % composition Carbon | Hydrogen | Chlorine |
|---|---|---|---|---|---|---|---|---|---|---|---|---|
| 11 | 4-methylphenol (108) | methyl 4-methylcyclohex-3-ene-1-carboxylate (61.6) | Fulmont 237 ® (5.0) | 150 | 6 | 2-(4-methyl-1-carbomethoxycyclohexyl)-4-methylphenol and 2-(1-methyl-4-carbomethoxycyclohexyl)-4-methylphenol | 160-70/0.3 | 141-3 | $C_{16}H_{23}O_3$ | 72.95 73.25 | 8.75 8.45 | |
| | | | | | | | | 134-6 | $C_{16}H_{22}O_3$ | 72.99 73.25 | 8.75 8.45 | |
| 12 | 4-methylphenol (540) | dimethyl 2-methylenebutanedioate (100) | Fulmont 237 ® (25) | 125 | 18 | dimethyl 2-(2-hydroxy-5-methylphenyl)methylbutanedioate → NaOH → 2-(2-hydroxy-5-methylphenyl)methylbutanedioic acid | | 115-6 | $C_{15}H_{20}O_5 \cdot H_2O$ | 60.88 60.39 | 7.58 7.43 | |
| 13 | 2,6-dimethylphenol (122) | methyl methacrylate (28.4) | Fulmont 237 ® (10) | 120 | 24 | methyl 2-(4-hydroxy-3,5-dimethylphenyl)-2-methylpropanoate | 156-64/0.3 | 40-2 | $C_{16}H_{24}O_3$ | 72.70 72.69 | 9.01 9.15 | |

-continued

| EXAMPLE | Phenol (parts) | Alkylating Agent (parts) | Catalyst (parts) | Reaction Temp. °C. | Reaction Time hours | Products | bp/pressure °C./mb | m.p. °C. | Molecular Formula | Found & required % composition Carbon | Hydrogen | Chlorine |
|---|---|---|---|---|---|---|---|---|---|---|---|---|
| 14 | 2,4-dimethylphenol, OH with CH₃ at 2- and 4- positions (122) | CH₂=C(CH₃)–CO₂CH₃ (28.4) | Fulmont 237 ® (10) | 120 | 24 | 2-hydroxy-3,5-dimethylphenyl derivative with CO₂CH₃ then NaOH → CO₂H | 148–52/0.3 | 159–62 | C₁₅H₂₂O₃ | 71.98 / 71.97 | 8.86 / 8.86 | |
| 15 | 4-ethylphenol (122) | CH₂=C(CH₃)–CO₂CH₃ (47) | Fulmont 237 ® (5.0) | 150 | 18 | 2-hydroxy-5-ethylphenyl derivative CO₂CH₃ then NaOH → CO₂H | 168–78/0.65 | 112–5 | C₁₅H₂₂O₃ | 71.84 / 71.97 | 8.88 / 8.86 | |
| 16 | 4-isopropylphenol (136) | CH₂=C(CH₃)–CO₂CH₃ (47) | Fulmont 237 ® (5.0) | 150 | 18 | 2-hydroxy-5-isopropylphenyl derivative CO₂CH₃ then NaOH → | 171–4/0.65 | | C₁₇H₂₆O₃ | 73.62 / 73.35 | 9.37 / 9.41 | |

-continued
| EXAMPLE | Phenol (parts) | Alkylating Agent (parts) | Catalyst (parts) | Reaction Temp. °C. | Reaction Time hours | Products | bp/pressure °C./mb | m.p. °C. | Molecular Formula | Found & required % composition Carbon | Hydrogen | Chlorine |
|---|---|---|---|---|---|---|---|---|---|---|---|---|
| 17 | 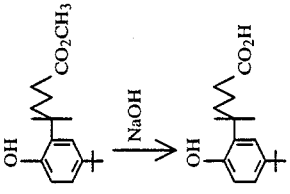 (75) | 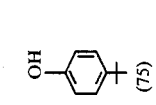 (28.4) | Fulmont 237 ® (5.0) | 125 | 20 |  | | 142–5 | $C_{16}H_{24}O_3$ | 72.97 72.69 | 9.30 9.15 | |
| | | | | | | 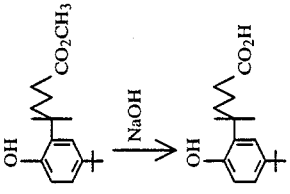 | | 111–4 | $C_{17}H_{26}O_3$ | 73.23 73.35 | 9.49 9.41 | |
| 18 | 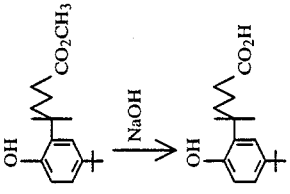 (71.2) | 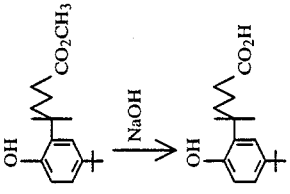 (61.6) | Fulmont 237 ® (5.0) | 150 | 7 | 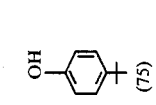 | 164–6/ 0.65 | 113–5 | $C_{21}H_{32}O_3$ | 75.64 75.86 | 9.67 9.70 | |
| | | | | | |  | | | | | | |
| | | | | | | 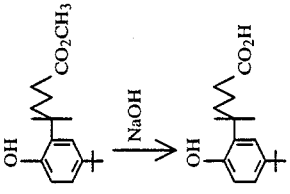 | | 161–3 | $C_{20}H_{30}O_3$ | 75.54 75.43 | 9.64 9.49 | |

-continued

| EXAMPLE | Phenol (parts) | Alkylating Agent (parts) | Catalyst (parts) | Reaction Temp. °C. | Reaction Time hours | Products | bp/pressure °C./mb | m.p. °C. | Molecular Formula | Found & required % composition Carbon | Hydrogen | Chlorine |
|---|---|---|---|---|---|---|---|---|---|---|---|---|
| 19 | 2-chlorophenol (64) | CH₂=CHCH(CO₂CH₃) (14.2) | Fulmont 237 ® (5.0) | 125 | 24 | 3-chloro-2-hydroxyphenyl-CH(CH₃)CO₂CH₃ and 3-chloro-4-hydroxyphenyl-CH(CH₃)CO₂CH₃ | 214-8/ 13 | 48-50 | C₁₄H₁₉ClO₃ | 62.01 62.10 | 7.18 7.07 | 13.36 13.09 |
| 20 | 4-chlorophenol (64) | CH₂=CHCH(CO₂CH₃) (14.2) | Fulmont 237 ® (5.0) | 150 | 24 | 4-chloro-2-hydroxyphenyl-CH(CH₃)CO₂CH₃ | 172-5/ 0.5 | 80-2 | C₁₄H₁₉ClO₃ | 62.15 62.10 | 7.10 7.07 | 12.95 13.09 |

EXAMPLE 21

(a) 12.5 Parts of methyl 5-(2-hydroxy-5-methylphenyl)-5-methyl-hexanoate prepared as described in Example 10, 14.2 parts of methyl 5-methyl-hex-5-enoate, and 1.0 parts of p-toluene sulphonic acid were heated on a steam-bath for 8 days. The reaction mixture after dilution with ether was washed with 2N sodium hydroxide solution, water, and evaporated.

Distillation of the residual oil gave after a fraction $b_{0.4}$ up to 200° C., bis-2,6-(5-methoxycarbonyl-2-methyl-pent-2-yl)-4-methyl-phenol $b_{0.4}$ 206°–10° C. and m.p. 55°–7° C. from 40°–60° C. petroleum-ether with the following percentage composition by weight.

|  | Carbon | Hydrogen |
|---|---|---|
| Found | 70.25 | 9.01 |
| Calculated for $C_{23}H_{36}O_5$ | 70.38 | 9.24 |

(b) Hydrolysis of bis-2,6-(2-methoxycarbonyl-2-methyl-pent-2-yl)-4-methyl-phenol from 21a above with aqueous potassium hydroxide gave the corresponding di-acid m.p. 138°–40° C. after crystallisation from 40°–60° C. petroleum-ether containing a little ether.

|  | Carbon | Hydrogen |
|---|---|---|
| Found | 69.38 | 9.13 |
| Calculated for $C_{21}H_{32}O_5$ | 69.20 | 8.85 |

EXAMPLE 22

37.8 Parts of bis-2,4-(5-methoxycarbonyl-2-methyl-pent-2-yl)phenol from Example 8, 28.4 parts of methyl 5-methyl-hex-5-enoate, and 3.0 parts of p-toluene sulphonic acid were heated on a steam-bath for 48 hours. The work up followed Example 21a and gave on distillation tris-2,4,6-(5-methoxycarbonyl-2-methyl-pent-2-yl)-phenol $b_{0.3}$ 230°–42° C., contaminated with 10% of the bis-2,4-diester. The impure triester was hydrolysed with potassium hydroxide and gave pure tris-2,4,6-(5-carboxy-2-methyl-pent-2-yl)-phenol with m.p. 156°–60° C. after crystallisation from water, and the following percentage composition by weight.

|  | Carbon | Hydrogen |
|---|---|---|
| Found | 67.61 | 8.89 |
| Calculated for $C_{27}H_{42}O_7$ | 67.76 | 8.84 |

EXAMPLE 23

(a) 94 Parts of phenol, 35.4 parts of dimethyl prenyl phosphonate, and 5.0 parts of Fulmont 237® were stirred at 125° C. for 15 hours. After the reaction mixture had been filtered, and the excess of phenol distilled off under reduced pressure, the residual oil was taken up in a mixture of ether and 40°–60° C. petroleum-ether. This solution after storage at 0° C. yielded dimethyl-3-(4-hydroxyphenyl)-3-methyl-butanephosphonate m.p. 98°–101° C. with the following percentage composition by weight.

|  | Carbon | Hydrogen | Phosphorus |
|---|---|---|---|
| Found | 57.41 | 7.83 | 11.38 |
| Calculated for $C_{13}H_{21}O_4P$ | 57.56 | 7.75 | 11.07 |

(b) 3.0 Parts of dimethyl-3-(4-hydroxyphenyl)-3-methyl-butane phosphonate from Example 23a and 30 parts of 48% hydrobromic acid were heated on a steam-bath for 1 hour and the volatiles then removed at 80° C. under reduced pressure. Crystallisation of the residual solid from water gave 3-(4-hydroxyphenyl)-3-methyl-butane phosphonic acid m.p. 192°–5° C. with the following percentage composition by weight.

|  | Carbon | Hydrogen | Phosphorus |
|---|---|---|---|
| Found | 54.01 | 7.06 | 12.52 |
| Calculated for $C_{11}H_{17}O_4P$ | 54.32 | 6.99 | 12.34 |

EXAMPLE 24

94 Parts of phenol, 26 parts of diethyl 2-ethoxycarbonyl-5-methyl-hex-4-ene-2-phosphonate, and 5.0 parts of Fulmont 237® were stirred at 110° C. for 24 hours, and then filtered free of catalyst. After removing excess phenol, short-path distillation of the residue at 0.13 mb yielded a mixture of diethyl 5-(2 and 4-hydroxyphenyl)-2-ethoxycarbonyl-5-methyl-hexane-2-phosphonate with the following percentage composition by weight.

|  | Carbon | Hydrogen | Phosphorus |
|---|---|---|---|
| Found | 60.14 | 8.16 | 7.73 |
| Calculated for $C_{20}H_{36}O_6P$ | 60.15 | 8.27 | 7.51 |

A 10 part sample of this mixture was separated by preparative H.P.L.C. after a single injection onto a column of 300 parts silica previously deactivated with 6% ethanol in hexane. The ortho-substituted isomer was obtained by elution with 5% ethanol in hexane and had m.p. 78°–80° C. after crystallisation from 40°–60° C. petroleum-ether containing a little ether at 0° C. The parasubstituted isomer was then obtained with dichloromethane solvent and had m.p. 86°–9° C. after crystallisation from 40°–60° C. petroleum-ether containing a little ether.

The diethyl 2-ethoxycarbonly-5-methyl-hex-4-ene-2-phosphonate used in this reaction was prepared by the following procedure. 4.8 Parts of sodium metal were dissolved in 200 parts of absolute ethanol and to this solution was added 50 parts of diethyl 1-ethoxycarbonyl-ethylphosphonate. To this stirred reaction mixture at room temperature was added 31.3 parts of 2-bromo-2-methyl-but-3-ene dropwise over 1 hour. On completion of the addition stirring was continued for 1 hour at room temperature and then for 2 hours at 60° C. After cooling, the reaction mixture was filtered free of sodium bromide and the filtrate concentrated under reduced pressure to remove ethanol. The residual oil was taken up in ether, and the ether solution washed with water and evaporated. Fractional distillation of the residue gave diethyl 1-ethoxycarbonyl-4-methyl-pent-3-ene-1-phosphonate $b_{0.3}$ 126°–34° C. with the following percentage composition by weight.

|  | Carbon | Hydrogen | Phosphorus |
|---|---|---|---|
| Found | 54.87 | 9.17 | 9.84 |
| Calculated for $C_{14}H_{27}O_5P$ | 55.08 | 8.85 | 9.83 |

EXAMPLE 25

24.4 Parts of 2,6-xylenol, 98 parts of 98% sulphuric acid, 18 parts of water, and 17.8 parts of dimethyl prenyl phosphonate were stirred at room temperature for 4 days, and then poured into 1000 parts of water. The oil which separated was extracted with ether and the ether solution washed successively with water, potassium bicarbonate solution, and water. After evaporation of the ether, distillation of the residual oil gave dimethyl 3-(4-hydroxy-3,5-dimethylphenyl)-3-methyl-butane phosphonate $b_{0.4}$ 200°-5° C., which after crystallisation from 40°-60° C. petroleum-ether containing ether gave crystals m.p. 89°-91°. with the following percentage composition by weight.

|  | Carbon | Hydrogen | Phosphorus |
|---|---|---|---|
| Found | 59.81 | 8.67 | 10.34 |
| Calculated for $C_{15}H_{25}O_4P$ | 59.98 | 8.39 | 10.31 |

EXAMPLE 26

(a) Similarly prepared according to the procedure of Example 25 and using 35.6 parts of 2,6-diisopropylphenol in place of the 2,6-xylenol was dimethyl 3-(4-hydroxy-3,5-diisopropylphenyl)-3-methyl-butane phosphonate with $b_{0.3}$ 180°-204° C., m.p. 81°-3° C., and percentage composition by weight of

|  | Carbon | Hydrogen | Phosphorus |
|---|---|---|---|
| Found | 64.22 | 9.29 | 9.00 |
| Calculated for $C_{19}H_{33}O_4P$ | 64.04 | 9.27 | 8.70 |

(b) Dimethyl 3-(4-hydroxy-3,5-diisopropylphenyl)-3-methylbutane phosphonate from Example 26a was hydrolised by the procedure of Example 23b to give 3-(4-hydroxy-3,5-di-isopropylphenyl)-3-methyl-butane phosphonic acid m.p. 179°-82° C. after crystallisation from carbon tetrachloride containing a little 40°-60° C. petroleum-ether.

|  | Carbon | Hydrogen | Phosphorus |
|---|---|---|---|
| Found | 59.58 | 8.55 | 8.86 |
| Calc. for $C_{17}H_{29}O_4P.H_2O$ | 58.95 | 8.95 | 8.95 |

EXAMPLE 27

12.8 Parts of 2,6-dichlorophenol, 14.2 parts of methyl 5-methyl-hex-5-enoate, 130 parts of 98% sulphuric acid, and 24 parts of methanol were stirred and heated on a steam-bath for 24 hours and the reaction mixture then worked up as in Example 25. Distillation gave methyl 5-(3,5-dichloro-4-hydroxyphenyl)-5-methyl-hexanoate $b_{0.5}$ 140°-60° C. and m.p. 101°-3° C., with the following percentage composition by weight.

|  | Carbon | Hydrogen | Chlorine |
|---|---|---|---|
| Found | 55.18 | 6.04 | 23.07 |
| Calculated for $C_{14}H_{18}Cl_2O_3$ | 55.09 | 5.94 | 23.24 |

Examples 28 to 43 in the following table still further exemplify the process by which phenols are functionally alkylated.

| EXAMPLE | Phenol (parts) | Alkylating Agent (parts) | Catalyst (parts) | Reaction Temp. °C. | Reaction Time Hrs. | Products | bp/pressure °C./mb | m.p. °C. | Molecular Formula | Found & required % composition Carbon | Hydrogen | Phosphorus |
|---|---|---|---|---|---|---|---|---|---|---|---|---|
| 28 |  OH / CH₃ (108) |  PO(OCH₃)₂ (23.4) | Fulmont 237 ® (5.0) | 120 | 26 | 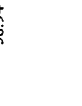 OH / PO(OCH₃)₂ / CH₃ | | 119-21 | C₁₄H₂₃O₄P | 58.96 58.94 | 8.07 8.07 | 10.72 10.52 |
| 29 |  OH (94) |  PO(OC₂H₅)₂ (27.6) | Fulmont 237 ® (5.0) | 110 | 18 |  HO— —PO(OC₂H₅)₂ | 200/0.13 short-path distn. | | C₂₀H₃₅O₄P | 64.83 64.86 | 9.63 9.46 | 8.19 8.37 |
| 30 |  OH (94) |  OH (78) | Fulmont 237 ® (5.0) | 110-20 | 24 | 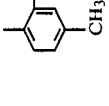 HO— —OH | 178-80/0.065 | | C₁₆H₂₆O₂ | 76.60 76.75 | 10.68 10.47 | |
| 31 |  OH / CH₃ (108) |  OH (31.2) | Fulmont 237 ® (5.0) | 125 | 18 |  OH / OH / CH₃ | 175-82/0.3 | | C₁₇H₂₈O₂ | 77.22 78.24 | 10.67 10.41 | |
| 32 |  OH (94) |  OCOCH₃ (88) | Fulmont 237 ® (5.0) | 110 | 24 | 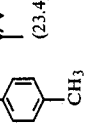 HO— —OCOCH₃ | 175-90/0.3 | | C₁₈H₂₈O₃ | 74.00 73.93 | 9.90 9.65 | |
| 33 |  OH (47) |  Br (11.0) | Fulmont 237 ® (2.5) | 110 | 6 |  HO— —Br | 166-70/0.13 | | C₁₆H₂₅BrO | 61.29 61.34 | 8.00 7.98 | |

| EXAMPLE | Phenol (parts) | Alkylating Agent (parts) | Catalyst (parts) | Reaction Temp. °C. | Reaction Time Hrs. | Products | bp/pressure °C./mb | m.p. °C. | Molecular Formula | Found & required % composition Carbon | Hydrogen | Nitrogen |

-continued

| | | | | | | |
|---|---|---|---|---|---|---|
| 34a | OH-C6H4-CH(NO2) chain (47) | Fulmont 237 ® (7.5) | 110-20 | OH-C6H4-CH(NO2) chain (2.5) 4 | | C16H25NO3 | 68.59 9.02 5.01 / 68.79 9.02 5.01 |
| | | | | HO-C6H4-CH(NO2) chain (para) | 186-200/ 0.07 | C16H25NO3 | 68.81 9.28 4.93 / 68.79 9.02 5.01 |

EXAMPLE 34b

The 3,7-dimethyl-1-nitro-oct-6-ene used to alkylate phenol in Example 34a was prepared:-

To a stirred solution of 13.3 parts of anhydrous phloroglucinol, 13.3 parts of urea and 12.0 parts of sodium nitrite in 200 parts of dimethylformamide was added 21.9 parts of citronellyl bromide dropwise keeping the temperature below 25° C. On completion of the addition stirring was continued a further 48 hours before pouring the reaction mixture into water. The organic phase which separated was ether extracted, and the extract washed with water and evaporated. Fractional distillation of the residue gave 4.8 parts of the citronellol $b_{16}$ up to 110° C. followed by 8.2 parts of 3,7-dimethyl-1-nitro-oct-6-ene $b_{16}$ 130°–2° C. with the following percentage composition by weight.

| EXAMPLE | Phenol (parts) | Alkylating Agent (parts) | Catalyst (parts) | Reaction Temp. °C | Reaction Time Hrs. | Products | bp pressure °C./mb | m.p. °C | Molecular Formula | Found & required % composition | | |
|---|---|---|---|---|---|---|---|---|---|---|---|---|
| | | | | | | | | | | Carbon | Hydrogen | Phosphorus |
| 35 | OH-C6H5 (94) | OCOCH3 alkene (25.6) | Fulmont 237 ® (5.0) | 150 | 2 | HO-C6H4-CH(CH3)CH2CH2-OCOCH3 | 154-60/0.65 | | C13H18O3 | 71.33 / 70.24 | 8.24 / 8.16 | |
| | | | | | | | | | | Found / Calculated for C10H19NO2: Carbon 64.47/64.83, Hydrogen 10.57/10.30, Nitrogen 7.32/7.56 | | |
| 36 | OH-C6H5 (94) | ketone (25.2) | Fulmont 237 ® (5.0) | 110 | 18 | HO-C6H4-C(CH3)CH2-C(=O)CH3 | 150/0.3 short-path distn | | C14H20O2 | 76.70 / 76.33 | 9.08 / 9.15 | |
| 37 | OH-C6H5 (94) | ketone (12.6) | Al(OPh)3 from Al (1.0) | 125 | 40 | OH-o-C6H4-C(CH3)CH2-C(=O)CH3 | | | C14H20O2 | 76.25 / 76.33 | 9.03 / 9.15 | |
| 38 | OH-C6H5 (94) | methylcyclohexenyl ketone (13.8) | Fulmont 237 ® (5.0) | 110 | 3 | HO-C6H4-cyclohexyl-C(=O)CH3 | 188-94/0.8 | 129-31 | C15H20O2 | 77.82 / 77.55 | 8.84 / 8.68 | |
| | | | | | | HO-C6H4-cyclohexyl-O-CH2CH3 | | 126-8 | C15H20O2 | 76.95 / 77.55 | 8.75 / 8.68 | |
| 39 | OH-C6H5 (94) | CN alkene (16.0) | Fulmont 237 ® (5.0) | 150 | 20 | HO-o-C6H4-C(CH3)CH2-CN | 218/13 | 90-2 | C13H17NO | 77.08 / 76.81 | 8.56 / 8.43 | 6.65 / 6.89 |
| | | | | | | HO-C6H4-C(CH3)CH2-CN | | | C13H17NO | 77.07 / 76.81 | 8.50 / 8.43 | 6.88 / 6.89 |

-continued

| # | Reactant 1 | Reactant 2 | Catalyst | Temp | Time (h) | Product | bp (°C/mm) | mp (°C) | Formula | C calc/found | H calc/found | N calc/found |
|---|---|---|---|---|---|---|---|---|---|---|---|---|
| 40 | phenol (OH-C₆H₅) (94) | 4-methyl-1-cyanocyclohexene (24.2) | Fulmont 237® (5.0) | 165 | 48 | 4-(4-hydroxyphenyl)-4-methylcyclohexanecarbonitrile | 252-8/13 | | C₁₄H₁₇NO | 78.48 / 78.10 | 8.18 / 7.96 | 6.08 / 6.51 |
| 41 | phenol (94) | ethyl 2-cyano-3-methylbut-2-enoate with CO₂C₂H₅/CN (18.1) | Fulmont 237® (5.0) | 110 | 20 | o-hydroxyphenyl substituted ester with CO₂C₂H₅/CN | 200/0.13 Short-path distn | | C₁₆H₂₁NO₃ | 70.07 / 69.79 | 8.24 / 7.69 | 4.68 / 5.09 |
| 42 | phenol (94) | aminoalcohol·HCl (NH₂·HCl) (18.1) | Fulmont 237® (5.0) | 110 | 20 | o-hydroxyphenyl amine (NH₂) | 198/16 | 96–8 | C₁₄H₂₃NO | 76.00 / 75.97 | 10.22 / 10.47 | 6.38 / 6.33 |
| | | | | | | 4-hydroxyphenyl amine (NH₂) | | 119–22 | C₁₄H₂₃NO | 76.27 / 75.97 | 10.72 / 10.47 | 6.28 / 6.33 |
| 43 | phenol (94) | NHCOCH₃ derivative (18.7) | Fulmont 237® (5.0) | 110 | 8 | 4-hydroxyphenyl acetamide (NHCOCH₃) | 217-25/0.07 | 105–7 | C₁₆H₂₅NO₂ | 73.07 / 72.97 | 9.45 / 9.57 | 5.30 / 5.32 |

EXAMPLE 44

Into 35.0 parts of methyl 5-(4-hydroxy-3-methyl-phenyl)-5-methyl-hexanoate from Example 9, 2.0 parts of 98% sulphuric acid, and 200 parts of toluene, was passed isobutylene for 2 hours at 75° C. After washing the toluene solution with 10% sodium hydroxide solution and then water, the toluene was stripped off and the residue distilled to give methyl 5-(3-t-butyl-4-hydroxy-5-methylphenyl)-5-methyl-hexanoate $b_{0.3}$ 168°–72° C. with the following percentage composition by weight.

|  | Carbon | Hydrogen |
| --- | --- | --- |
| Found | 74.71 | 10.08 |
| Calculated for $C_{19}H_{30}O_3$ | 74.47 | 9.87 |

EXAMPLE 45

Following the same procedure described in Example 44 and using methyl 5-(2-hydroxy-5-iso-propyl-phenyl)-5-methyl-hexanoate from Example 16 in place of methyl 5-(4-hydroxy-3-methyl-phenyl)-5-methyl-hexanoate, methyl 5-(3-t-butyl-2-hydroxy-5-isopropyl-phenyl)-5-methyl-hexanoate $b_{0.3}$ 152°–4° C. was obtained with the following percentage by weight.

|  | Carbon | Hydrogen |
| --- | --- | --- |
| Found | 75.58 | 10.31 |
| Calculated for $C_{21}H_{34}O_3$ | 75.41 | 10.25 |

EXAMPLE 46

50 Parts of methyl 5-(2-hydroxy-5-methylphenyl)-5-methyl-hexanoate, 30 parts of isobutylene, 2.0 parts of p-toluene sulphonic acid, and 160 parts of cyclohexane were sealed into an autoclave and stirred at 100° C. for 24 hours. After washing the discharged reaction mixture with 10% sodium hydroxide, followed by water, the residual oil obtained after evaporation was chromatographed on a column prepared from 500 parts silica and 40°–60° C. petroleum-ether as solvent. Elution with petroleum-ether containing 5% ether yielded pure methyl 5-(3-t-butyl-2-hydroxy-5-methylphenyl)5-methyl-hexanoate $b_{0.13}$ 142°–50° C. with the following percentage composition by weight.

|  | Carbon | Hydrogen |
| --- | --- | --- |
| Found | 74.94 | 9.91 |
| Calculated for $C_{19}H_{30}O_3$ | 74.47 | 9.87 | the above ester after alkaline hydrolyis gave after crystallisation from 40°–60° C. petroleum-ether 5-(3-t-butyl-2-hydroxy-5-methylphenyl)-5-methyl-hexanoic acid m.p. 99°–101° C. with the following percentage composition by weight.

|  | Carbon | Hydrogen |
| --- | --- | --- |
| Found | 73.35 | 9.85 |
| Calculated for $C_{18}H_{28}O_3$ | 73.93 | 9.65 |

EXAMPLE 47

Methyl 5-(3,5-di-t-butyl-4-hydroxyphenyl)-5-methyl-hexanoate prepared with methyl 5-(4-hydroxyphenyl)-5-methyl-hexanoate from Example 1a and isobutylene by the method of Example 44 had after crystallisation from 40°–60° C. petroleum-ether m.p. 71°–2° C. and the following percentage composition by weight.

|  | Carbon | Hydrogen |
| --- | --- | --- |
| Found | 75.96 | 10.64 |
| Calculated for $C_{22}H_{36}O_3$ | 75.81 | 10.41 |

EXAMPLE 48

Methyl 5-(3,5-di-t-butyl-2-hydroxyphenyl)-5-methyl-hexanoate $b_{0.7}$ 152°–8° C. was prepared and purified by the method described in Example 46 starting with methyl 5-(5-t-butyl-2-hydroxyphenyl)-5-methyl-hexanoate from Example 17 and isobutylene.

|  | Carbon | Hydrogen |
| --- | --- | --- |
| Found | 75.78 | 10.47 |
| Calculated for $C_{22}H_{36}O_3$ | 75.81 | 10.41 |

EXAMPLE 49

Into a solution of 20 parts cis and trans 4-methoxycarbonyl-1-(p-hydroxyphenyl)-1-methyl-cyclohexane from Example 2, 2.0 parts of 98% sulphuric acid, and 50 parts of benzene at 70° C. was passed isobutylene gas for 3 hours. At the end of this period the cooled solution was diluted with ether washed with sodium bicarbonate solution and evaporated. The residual oil was then diluted with 40°–60° C. petroleum-ether and gave as a first crop of crystals cis-[4-methoxycarbonyl-1-(3,5-di-t-butyl-4-hydroxyphenyl)]-1-methyl-cyclohexane m.p. 152°–5° C. with the following percentage composition by weight.

|  | Carbon | Hydrogen |
| --- | --- | --- |
| Found | 76.79 | 10.07 |
| Calculated for $C_{23}H_{36}O_3$ | 76.62 | 10.07 |

The mother liquors from the above crystallisation yielded a second crop of crystals m.p. 92°–5° C. which after crystallisation from methanol gave pure trans-[4-methoxycarbonyl-1-(3,5-di-t-butyl-4-hydroxyphenyl)]-1-methyl-cyclohexane m.p. 95°–7° C. with the following percentage composition by weight.

|  | Carbon | Hydrogen |
| --- | --- | --- |
| Found | 76.90 | 10.02 |
| Calculated for $C_{23}H_{36}O_3$ | 76.62 | 10.07 |

EXAMPLE 50

27.0 Parts of trans-[4-methoxycarbonyl-1-(3,5-di-t-butyl-4-hydroxy-phenyl]-1-methyl-cyclohexane, 4.4 parts of hexane-1,6-diol, and 0.3 parts of lithamide were stirred at 80° C. and 13 mb pressure for 24 hours. After the addition of 2.0 parts of glacial acetic acid, the reaction mixture was diluted with ether washed with water and evaporated. The residual solid after crystallisation from methanol gave bis-[4-methyl-trans-(4-(3,5-di-t-butyl-4-hydroxyphenyl)-cyclohexane-1-carboxylic acid] ester of hexane-1,6-diol m.p. 120°–2° C. with the following percentage composition by weight.

|  | Carbon | Hydrogen |
|---|---|---|
| Found | 77.80 | 9.84 |
| Calculated for $C_{50}H_{78}O_6$ | 77.47 | 10.14 |

Examples 51 to 53 in the following table further exemplify esters similarly prepared according to the procedure of Example 50.

| EXAMPLE | Phenol (parts) | Alcohol (parts) | Catalyst (parts) | Reaction Temp. °C. | Reaction Time Hrs. | Product | bp/pressure °C./mb | Molecular Formula | Found & required % composition Carbon | Hydrogen |
|---|---|---|---|---|---|---|---|---|---|---|
| 51 |  (10.2) | HO(CH$_2$)$_6$OH (1.9) | LiNH$_2$ (0.1) | 150 | 7 |  | 250/0.13 Short-path distn. | C$_{42}$H$_{66}$O$_6$ | 75.58 75.63 | 10.23 9.97 |
| 52 | 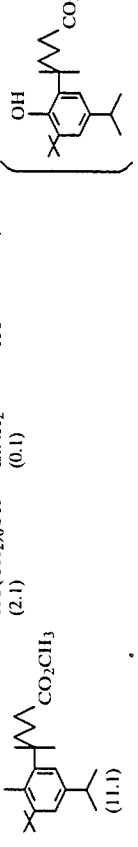 (11.1) | HO(CH$_2$)$_6$OH (2.1) | LiNH$_2$ (0.1) | 150 | 7 |  | 250/0.7 Short-path distn. | C$_{46}$H$_{74}$O$_6$ | 75.23 75.40 | 10.26 10.26 |
| 53 |  (16.0) | HO(CH$_2$)$_6$OH (2.7) | LiNH$_2$ (0.1) | 150 | 8 | 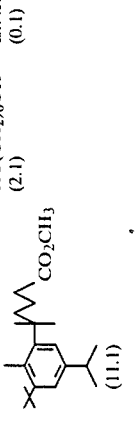 | 300-15/0.7 | C$_{48}$H$_{78}$O$_6$ | 76.98 76.75 | 10.24 10.47 |

EXAMPLE 54

2.0 Parts of 5-(3-t-butyl-2-hydroxy-5-methyl-phenyl)-5-methylhexanoic acid and 2.0 parts thionyl chloride in 25 parts of toluene were stored for 2 hours at room temperature. The toluene and other volatiles were then stripped off at room temperature and $^{16}$ mb pressure. To the residue was then added 10 parts of 1,1,3,3-tetramethyl-butylamine and this mixture heated for 3 hours on a steam-bath. After diluting the reaction mixture with ether, the ether solution was washed successively with dilute hydrochloric acid, water, dilute sodium hydroxide, and water. Evaporation of the ether and crystallisation from 60°–80° C. petroleum-ether gave 5-(3-t-butyl-2-hydroxy-5-methylphenyl)-5-methyl-hexanoic acid amide of 1,1,3,3-tetramethylbutylamine m.p. 110°–2° C. with the following percentage composition by weight.

|  | Carbon | Hydrogen | Nitrogen |
|---|---|---|---|
| Found | 77.30 | 11.24 | 3.40 |
| Calculated for $C_{26}H_{45}NO_2$ | 77.37 | 11.24 | 3.47 |

EXAMPLE 55

9.0 Parts of 5-(3-t-butyl-2-hydroxy-5-methyl-phenyl)-5-methyl-hexanoic acid from Example 46 and 30.0 parts of n-dodecylamine were stirred at 175° C. for 24 hours. After distilling off the excess dodecylamine there was obtained 5-(3-t-butyl-2-hydroxy-5-methyl-phenyl)-5-methyl-hexanoic acid amide of n-dodecylamine $b_{0.3}$ 246° C. and m.p. 43°–5° C. with the following percentage composition by weight.

|  | Carbon | Hydrogen | Nitrogen |
|---|---|---|---|
| Found | 78.64 | 11.84 | 2.93 |
| Calculated for $C_{30}H_{53}NO_2$ | 78.43 | 11.54 | 3.05 |

EXAMPLE 56

14.6 Parts of 5-(3-t-butyl-2-hydroxy-5-methyl-phenyl)-5-methyl-hexanoic acid from Example 46 and 2.9 parts of hexamethylene diamine were heated at 150° C. for 24 hours. The solid obtained on cooling was crystallised from toluene and gave bis-5-(3-t-butyl-2-hydroxy-5-methyl-phenyl)-5-methyl-hexanoic acid amide of 1,6-diaminohexane m.p. 139°–42° C. with the following percentage composition by weight.

|  | Carbon | Hydrogen | Nitrogen |
|---|---|---|---|
| Found | 76.17 | 10.08 | 4.19 |
| Calculated for $C_{42}H_{68}N_2O_4$ | 75.91 | 10.23 | 4.24 |

EXAMPLE 57

5.0 Parts of 5-(3-t-butyl-2-hydroxy-5-methyl-phenyl)-5-methyl-hexanoic acid from Example 46 and 20 parts of aniline were refluxed for 20 hours and then poured into an excess of hydrochloric acid. The oil which separated was extracted with ether and then washed successively with 2N hydrochloric acid, sodium bicarbonate solution and water. Evaporation of the ether gave a brown solid which was then passed through a column prepared from 100 parts of silica and 40°–60° C. petroleum-ether as solvent. Elution with the above solvent containing 10% of ether gave N-phenyl 5-methyl-5-(3-t-butyl-2-hydroxy-5-methyl-phenyl)-hexamide m.p. 122°–4° C. after crystallisation from 40°–60° C. petroleum ether containing a little ether.

|  | Carbon | Hydrogen | Nitrogen |
|---|---|---|---|
| Found | 78.06 | 9.09 | 3.50 |
| Calculated for $C_{24}H_{33}NO_2$ | 78.43 | 9.05 | 3.81 |

EXAMPLE 58

30.4 Parts of methyl salicylate, 28.4 parts of methyl 5-methyl-hex-5-enoate, 130 parts of 98% sulphuric acid, and 24 parts of methanol were stirred at room temperature for 4 days. The reaction mixture was worked up as described in Example 25 and gave on distillation methyl 2-hydroxy-5-(5-methoxycarbonyl-2-methyl-pent-2-yl)-benzoate $b_{0.3}$ 150°–2° C.

|  | Carbon | Hydrogen |
|---|---|---|
| Found | 65.27 | 7.65 |
| Calculated for $C_{16}H_{22}O_5$ | 65.29 | 7.53 | and methyl 2-hydroxy-3,5-bis-(5-methoxycarbonyl-2-methyl-pent-2-yl)benzoate $b_{0.1}$ 220° C.

|  | Carbon | Hydrogen |
|---|---|---|
| Found | 65.75 | 8.28 |
| Calculated for $C_{24}H_{36}O_7$ | 66.03 | 8.31 |

Alkaline hydrolysis of the above esters gave 5-(5-carboxy-2-methyl-pent-2-yl)-2-hydroxybenzoic acid m.p. 136°–8° C. and 3,5-bis-(5-carboxy-2-methyl-pent-2-yl)-2-hydroxybenzoic acid m.p. 161°–3° C. In a similar manner to Example 58 there can be obtained, Methyl 5-(6-amino-2-methyl-hept-2-yl)-2-hydroxy-benzoate (not distilled as polymerisation occurs on heating).

|  | Carbon | Hydrogen | Nitrogen |
|---|---|---|---|
| Found | 67.93 | 9.10 | 4.90 |
| Calculated for $C_{16}H_{25}NO_3$ | 68.79 | 9.02 | 5.01 |

5-(6-Amino-2-methyl-hept-2-yl)-2-hydroxybenzoic acid m.p. 182°–5° C.

|  | Carbon | Hydrogen | Nitrogen |
|---|---|---|---|
| Found | 64.58 | 8.97 | 5.00 |
| Calculated for $C_{15}H_{23}NO_3.H_2O$ | 63.58 | 8.89 | 4.94 |

Methyl · 2-hydroxy-5-(2-methyl-4-dimethylphosphono-but-2-yl)-benzoate $b_{0.1}$ 175° C.

|  | Carbon | Hydrogen | Phosphorus |
|---|---|---|---|
| Found | 54.20 | 7.30 | 9.08 |
| Calculated for $C_{15}H_{23}O_6P$ | 54.54 | 7.02 | 9.38 |

2-Hydroxy-5-(2-methyl-4-phosphono-but-2-yl)-benzoic acid m.p. 125°–35° C.

|  | Carbon | Hydrogen | Phosphorus |
|---|---|---|---|
| Found | 49.07 | 6.25 | 11.97 |

|  | Carbon | Hydrogen | Phosphorus |
|---|---|---|---|
| Calculated for $C_{12}H_{17}O_6P$ | 50.00 | 5.95 | 10.74 |

Methyl 4-hydroxy-3-(5-methoxycarbonyl)-2-methyl-pent-2-yl)benzoate m.p. 80°-2° C.

|  | Carbon | Hydrogen |
|---|---|---|
| Found | 65.45 | 7.68 |
| Calculated for $C_{16}H_{22}O_5$ | 65.29 | 7.53 |

EXAMPLE 59

To a stirred solution of 19.0 parts water, 0.5 parts 98% sulphuric acid, and 0.2 parts of sodium dodecylbenzene sulphonate was added 25.0 parts of methyl 5-(4-hydroxy-3-methylphenyl)-5-methyl-hexanoate from Example 9 and 1.0 parts of 80°-100° C. petroleum ether. The temperature of this stirred mixture was raised to 80° C. and then 4.4 parts of 40% formaldehyde solution added dropwise over 1 hour. On completing the addition the temperature was maintained at 80° C. for a further 2 hours before 100 parts of water were added. The organic phase was ether extracted, and the extract washed with sodium bicarbonate solution, water, and evaporated. Short-path distillation of the residue gave 11.0 parts of methyl 5-(4-hydroxy-3-methyl-phenyl)-5-methyl-hexanoate $b_{0.7}$ 150° (oven temperature) followed by bis-[2-hydroxy-5-(5-methoxycarbonyl-2-methyl-pent-2-yl)-3-methyl-phenyl]-methane $b_{0.7}$ 250° (oven temperature).

|  | Carbon | Hydrogen |
|---|---|---|
| Found | 72.55 | 8.69 |
| Calculated for $C_{31}H_{46}O_6$ | 72.63 | 8.65 |

EXAMPLE 60

In the manner described in Example 59 there was prepared from methyl 5-(2-hydroxy-5-methyl-phenyl)-5-methyl-hexanoate of Example 10, bis-2-hydroxy-3-(5-methoxycarbonyl-2-methyl-pent-2-yl)-5-methyl-phenyl-methane $b_{0.07}$ 284° C.

|  | Carbon | Hydrogen |
|---|---|---|
| Found | 72.75 | 8.30 |
| Calculated for $C_{31}H_{46}O_6$ | 72.63 | 8.65 |

EXAMPLE 61

12.2 Parts of 2,6-dimethylphenol, 5.3 parts of citronellyl n-butyl ether, and 1.0 parts of 70% perchloric acid in 30 parts of methylene chloride were stored at room temperature for 3 days. The reaction mixture after pouring into water was extracted with ether, and the ether solution washed with sodium bicarbonate solution, then water and evaporated. Distillation of the residual oil gave 1-n-butyloxy-7-(4-hydroxy-3,5-dimethyl-phenyl)-3,7-dimethyl-octane as a fraction with $b_{0.8}$, 168°-76° C.

|  | Carbon | Hydrogen |
|---|---|---|
| Found | 79.05 | 11.52 |
| Calculated for $C_{22}H_{38}O_2$ | 78.99 | 11.45 |

EXAMPLE 62

10.3 Parts of 4-(5-methoxycarbonyl-2-methyl-pent-2-yl)-phenol, 4.2 parts of citronellyl n-butyl ether, and 0.5 parts of 70% perchloric acid in 25 parts of methylene chloride were stored at room temperature for 4 days. The work-up followed Example 61 and gave on distillation 2-(8-n-butyloxy-2,6-dimethyl-oct-2-yl)-4-(5-methoxycarbonyl-2-methyl-pent-2-yl)-phenol with $b_{0.8}$, 228°-36° C.

|  | Carbon | Hydrogen |
|---|---|---|
| Found | 75.02 | 11.08 |
| Calculated for $C_{28}H_{48}O_4$ | 74.95 | 10.78 |

EXAMPLE 63

2.3 Parts of 4-n-decylphenol, 1.4 parts of methyl 5-methyl-hex-5-enoate, 0.25 of 70% perchloric acid, and 10 parts of methylene chloride were stored for 12 days at room temperature. The work up followed Example 61 and gave on distillation, methyl 5-(5-n-decyl-2-hydroxyphenyl)-5-methyl-hexanoate, $b_{0.8}$, 160°-7° C.

|  | Carbon | Hydrogen |
|---|---|---|
| Found | 76.66 | 10.80 |
| Calculated for $C_{24}H_{40}O_3$ | 76.55 | 10.71 |

EXAMPLE 64

5.0 Parts of 2-methyl-4-(5-methoxycarbonyl-2-methyl-pent-2-yl)-phenol, 2.4 parts of α-methylstyrene, and 0.5 parts of 70% perchloric acid in 25 parts of methylene chloride were reacted and worked up as described in Example 61. Distillation gave methyl 5-(3-cumyl-4-hydroxy-5-methyl-phenyl)5-methyl-hexanoate, $b_{0.7}$ 210°-4° C. as an oil with the following percentage composition by weight.

|  | Carbon | Hydrogen |
|---|---|---|
| Found | 78.22 | 8.75 |
| Calculated for $C_{24}H_{32}O_3$ | 78.78 | 8.89 |

EXAMPLE 65

27.2 Parts of 2-hydroxyacetophenone and 14.2 parts of methyl 5-methyl-hex-5-enoate were added at room temperature to a solution prepared from 32 parts methanol and 100 parts of sulphuric acid. After stirring for 3 days at room temperature the reaction mixture was poured into water and the organic phase extracted with ether. The ether extract, after washes with sodium bicarbonate solution and water, was evaporated. The residual was distilled and yielded a mixture of 2-hydroxy-3-(5-methoxycarbonyl-2-methyl-pent-2-yl)-acetophenone and 2-hydroxy-5-(5-methoxycarbonyl-2-methyl-pent-2-yl)-acetophenone.

|  | Carbon | Hydrogen |
| --- | --- | --- |
| Found | 69.31 | 8.19 |
| Calculated for $C_{16}H_{22}O_4$ | 69.04 | 7.97 |

EXAMPLE 66

Example 65 was repeated except that 19.8 parts of 2-hydroxybenzophenone were used in place of the 2-hydroxyacetophenone and the period was 5 days. Distillation gave a fraction $b_{0.7}$, 198°–204° C. which was a mixture of 2-hydroxy-3-(5-methoxycarbonyl2-methyl-pent-2-yl)-benzophenone and 2-hydroxy-5-(5-methoxycarbonyl-2-methyl-pent-2-yl)-benzophenone.

|  | Carbon | Hydrogen |
| --- | --- | --- |
| Found | 74.00 | 7.32 |
| Calculated for $C_{21}H_{24}O_4$ | 74.09 | 7.11 |

EXAMPLE 67

Methyl 5-(4-hydroxy-3-methylphenyl)-5-methyl-hexanoate obtained as described in Example 9 was transesterified with allyl alcohol using p-toluene sulphonic acid catalyst and gave allyl 5-(4-hydroxy-3-methylphenyl)-5-methyl-hexanoate, $b_{0.7}$, 182°–8° C.

|  | Carbon | Hydrogen |
| --- | --- | --- |
| Found | 73.69 | 8.66 |
| Calculated for $C_{17}H_{24}O_3$ | 73.88 | 8.75 |

EXAMPLE 68

The procedure of Example 67 was used to prepare cyclohexyl 5-(4-hydroxy-3-methylphenyl)-5-methyl-hexanoate, $b_{0.9}$, 200°–4° C. from cyclohexanol and methyl 5-(4-hydroxy-3-methylphenyl)-5-methyl-hexanoate.

|  | Carbon | Hydrogen |
| --- | --- | --- |
| Found | 75.03 | 9.41 |
| Calculated for $C_{20}H_{30}O_3$ | 75.43 | 9.50 |

EXAMPLE 69

To a stirred suspension of 2.0 parts lithium aluminium hydride in 100 parts of dry tetrahydrofuran was added 5.3 parts of 2-acetamido-6-(4-hydroxyphenyl)-6-methyl-heptane in 50 parts of dry tetrahydrofuran. After completion of the addition the reaction mixture was stirred a further 20 hours at room temperature before ethyl acetate was added to destroy excess lithium aluminium hydride. The reaction mixture was then poured into water and filtered free of solids. The aqueous phase and solids were extracted with ether and the ether solution washed with water and evaporated. The residual oil gave 2-N-ethylamino-6-(4-hydroxyphenyl)-6-methyl-heptane as a colourless oil following a short-path rotary distillation at 0.7 mb with an oven temperature of 190° C.

|  | Carbon | Hydrogen | Nitrogen |
| --- | --- | --- | --- |
| Found | 76.78 | 11.26 | 5.50 |
| Calculated for $C_{16}H_{27}NO$ | 77.06 | 10.91 | 5.62 |

EXAMPLE 70

To 10.0 parts of 5-(4-hydroxyphenyl)-5-methyl-hexanoic acid suspended in 75 parts of toluene was added 10.0 parts thionyl chloride. This mixture was warmed gently to 50° C. until all the suspended acid had passed into solution, and then set aside overnight at room temperature. The toluene and other volatiles were then removed at room temperature under reduced pressure, and the residue treated with 75 parts of 0.88 (g/cm³) aqueous ammonia. The organic phase was extracted with ether, and the ether solution washed with dilute hydrochloric acid followed by water and evaporated. The residue was taken up in dilute sodium hydroxide, and this solution after treatment with solid carbon dioxide yielded 5-(4-hydroxyphenyl)-5-methyl-hexanoic acid amide with m.p. 137°–9° C. after crystallisation from methanol containing a little ether.

|  | Carbon | Hydrogen | Nitrogen |
| --- | --- | --- | --- |
| Found | 70.48 | 8.57 | 6.03 |
| Calculated for $C_{13}H_{19}NO_2$ | 70.56 | 8.65 | 6.33 |

EXAMPLE 71

5.0 Parts of methyl 5-(4-hydroxyphenyl)-5-methyl-hexanoate and 50 parts of n-butylamine were sealed into a glass tube and heated at 200° C. for 24 hours. After cooling the reaction it was stripped of excess butylamine under reduced pressure and the residual oil gave after a short-path rotary distillation at 0.7 mb N-n-butyl-5-(4-hydroxyphenyl)-5-methyl-hexanoic acid amide.

|  | Carbon | Hydrogen | Nitrogen |
| --- | --- | --- | --- |
| Found | 73.47 | 9.99 | 4.82 |
| Calculated for $C_{17}H_{27}NO_2$ | 73.61 | 9.81 | 5.05 |

EXAMPLE 72

Example 71 was repeated using 50 parts of diethylamine in place of the n-butylamine and the heating period was 48 hours. From this reaction there was obtained N,N-diethyl-5-(4-hydroxyphenyl)-5-methyl-hexanoic acid amide with the following percentage composition by weight.

|  | Carbon | Hydrogen | Nitrogen |
| --- | --- | --- | --- |
| Found | 73.43 | 9.95 | 4.62 |
| Calculated for $C_{17}H_{27}NO_2$ | 73.61 | 9.81 | 5.05 |

EXAMPLES 73-5

Corrosion inhibitor activity for an active compound of formula I was demonstrated in the following way by the Aerated Solution Bottle Test and using a standard corrosive water made up as follows:
20 g. $CaSO_4\ 2H_2O$
15 g. $MgSO_4\ 7H_2O$
4.6 g. $NaHCO_3$ 7.7 g. CaCl$_2$ 6H$_2$O
45 gallons Distilled water Mild steel coupons, 5 cms.×2.5 cms. are scrubbed with pumice, immersed for one minute in hydrochloric acid and then rinsed, dried and weighed.

0.1 g. of the compound of formula I is dissolved in 100 ml of standard corrosive water to give a concentration of 100 ppm. A steel coupon is suspended in the solution, and the whole is stored in a bottle in a thermostat at 40° C. During the storage period, air is passed into the solution at 500 ml/minute, the passage of the air being screened from the steel coupon; any water losses by evaporation are replaced as they occur with distilled water from a constant head apparatus. After 48 hours, the steel coupon is removed, scrubbed with pumice, immersed for one minute in hydrochloric acid inhibited with 1% by weight of hexamine and then rinsed, dried and reweighed. A certain loss in weight will have occurred. A blank test i.e. immersion of a mild steel specimen in the test water in the absence of any potential corrosion inhibitor, is carried out with each series of test. The corrosion rates are calculated in milligrams of weight loss/sq. decimeter/day (m.d.d.) but for convenience the results are shown as percentage protection, which is defined as follows: % Protection=

$$\frac{\text{Corrosion rate for blank (in m.d.d.)} - \text{corrosion rate for sample (in m.d.d.)}}{\text{Corrosion rate for blank (in m.d.d.)}} \times 100$$

The results obtained are set out in Table 1.

TABLE 1

Mild Steel Corrosion inhibition of Compounds of Formula I in a Standard Corrosive Water

| Example | Compound | Corrosion Inhibition as % Protection at 100 p.p.m. |
|---|---|---|
| 73 | The product of Example 21b | 98 |
| 74 | The di-acid product Example 8 | 98 |
| 75 | The tri-acid product Example 22 | 100 |

The results in Table I show the effective mild corrosion inhibitory properties of the compound of formula I.

EXAMPLES 76-80

The corrosion resistance of an aqueous cutting fluid composition of the invention was assessed by the following procedures, which is a modification of the Institute of Petroleum Test 287. A 1% aqueous solution of the corrosion inhibitor under test is prepared containing sufficient triethanolamine (TEA) to bring its pH value to 9.

This solution is further diluted by factors of 2, 4, 8 and 16 and each of these solutions contacted with cast iron chips according to the method set forth in the IP 287 Test Procedure. The test is carried out using de-ionised water.

The visual assessment of the condition of the metal chips after exposure is in accordance with the following guidelines.

| Degree of rusting | Rating |
|---|---|
| no rusting | O |
| ≦5 small specks | T (trace) |
| ≦10% area rusted | M (moderate) |
| >10% area rusted | S (severe) |

The results obtained are set out in Table 2 and clearly show the effectivity of the compounds of formula 1.

TABLE 2

Cast Iron Corrosion Inhibition of Compounds of Formula I in Aqueous Cutting Fluids

| Example | Compound | % TEA for 1% of the Compound | pH | Dilution Ratio | % | Rust (Deionised water) |
|---|---|---|---|---|---|---|
| 76 | The product of Example 16 | 4.8 | 9.1 | 1:68 | 0.25 | T |
|  |  |  |  | 1:136 | 0.125 | S |
| 77 | The di-acid product of Example 8 | 5.2 | 9.0 | 1:64 | 0.25 | O |
|  |  |  |  | 1:128 | 0.125 | O |
|  |  |  |  | 1:256 | 0.062 | O |
| 78 | the tri-acid product of Example 22 | 3.6 | 9.1 | 1:22 | 1.0 | O |
|  |  |  |  | 1:44 | 0.5 | O |
|  |  |  |  | 1:88 | 0.25 | O |
|  |  |  |  | 1:180 | 0.125 | O |
|  |  |  |  | 1:360 | 0.062 | T-M |
| 79 | The product of Example 23b | 5.8 | 9.0 | 1:58 | 0.25 | O |
|  |  |  |  | 1:116 | 0.125 | M |
|  |  |  |  | 1:232 | 0.062 | S |
| 80 | The product of Example 26b | 3.9 | 9.0 | 1:82 | 0.25 | O |
|  |  |  |  | 1:164 | 0.125 | S |

*Dilution ratio is the ratio of triethanolamine + compound to water
% is % of compound in tested solution

EXAMPLE 81

The thermal antioxidant activity for an active compound of formula 1 in lubricating oil was assessed according to the Institute of Petroleum Test 229. The test oil, water, and copper catalyst coil, contained in a covered glass container, are placed in a bomb equipped with a pressure gauge. The bomb is charged with oxygen to a pressure of 90 psi, placed in a constant temperature oil-bath set at 150° C., and rotated axially at 100 rpm at an angle of 30° from the horizontal. The initial time in minutes for the test oil to react with a given volume of oxygen is measured, completion of time being indicated by a specific drop in pressure.

The results set out in Table 3 demonstrate how a compound of formula 1 can inhibit the oxidation of Rotary Vacuum Oil (RVO) and reduce the formation of acidic by-products when compared with RVO without such an additive.

TABLE 3

Thermal Oxidation Inhibition of Lubricating Oil by Compounds of Formula I

| Example | Compound | Total Acid No. (mg KOH/g.) | Standard Robot Life (min.) |
|---------|----------|---------------------------|----------------------------|
| Blank | RVO Basestock | 2.4 | 58 |
| 81 | RVO containing product from Example 57 | 0.28 | 228 |

What we claim is:

1. A compound having the formula

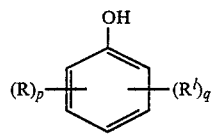  (I)

wherein p is 1, 2 or 3; and q is 0, 1 or 2 provided that $p+q \leq 3$; R is a group of the formula

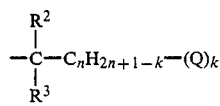  (II)

and when p is 2 or 3, each group R may be the same or different and is present in the 2-, 4- or 6-position; n is an integer from 2 to 30; K is 1 or 2; Q is —COOR$^4$ or —CONR$^4$R$^5$ wherein R$^4$ is (1) H; (2) a straight or branched chain alkyl having from 1 to 20 carbon atoms; (3) divalent straight or branched chain alkylene having 2-20 carbon atoms; (4) a straight or branched chain alkenyl group having from 3 to 20 carbon atoms, (5) a cycloalkyl group having from 3 to 12 carbon atoms; (6) an aryl group having from 6 to 10 carbon atoms which is unsubstituted or is substituted by a $C_1$-$C_4$ alkyl group; (7) an aralkyl group having from 7 to 13 carbon atoms; provided that when k is 2, the two carbon atoms to which the —COOR$^4$ groups are attached are not adjacent to one another; and R$^5$ is hydrogen or a straight or branched chain alkyl group having from 1 to 20 carbon atoms, or R$^4$ or R$^5$ together with the nitrogen atom to which they are each bonded may form a pyrrolidine, piperidine, morpholine or 2,5-dimethyl morpholine; R$^2$ and R$^3$ are the same or different and each is straight or branched chain alkyl group having from 1 to 5 carbon atoms and, when Q is CO$_2$R$^4$, either R$^2$ or R$^3$ is optionally substituted by a —CO$_2$R$^4$ group, the R$^4$ groups being independent, or R$^2$ or R$^3$ may be so linked to the residue $C_nH_{2n+1-k}$ that there is formed a $C_5$-$C_{12}$ cycloalkylene residue substituted by the group —(CO$_2$R$^4$)$_k$, the R$^4$ groups being independent, wherein R$^4$ and k are as previously defined; R$^1$ is a $C_1$-$C_{12}$ straight or branched chain alkyl group, a $C_7$-$C_9$ aralkyl group, halogen, CF$_3$, SH, SR$^{13}$, CO$_2$H, CO$_2$R$^{13}$, COR$^{13}$, COC$_6$H$_5$, CONH$_2$, CN, SO$_3$H, SO$_2$NH$_2$, PO(OH)$_2$, PO(OR$^{13}$)$_2$, or NO$_2$ wherein R$^{13}$ is a $C_1$-$C_4$ straight or branched chain alkyl group, and, when O is 2, each R$^1$ group may be the same or different; and provided that, when p is 1, R$^1$ is $C_1$-$C_{12}$ alkyl, R$^2$ and R$^3$ are $C_1$-$C_5$ alkyl, k is 1, O is —COOR$^4$ wherein R$^4$ is H, and q is as previously defined, then n is not 2; and further provided that when k is 2 and p is 1 and the group R is in the para-position to the phenolic OH, then in such case (a) when O is —COOR$^4$, R$^4$ is other than straight or branched chain alkyl and unsubstituted or substituted phenyl, and (b) when O is —CONR$^4$R$^5$, R$^4$ and R$^5$ are not both H;

or a salt thereof with an organic or inorganic acid or base.

2. A compound according to claim 1 and having the formula

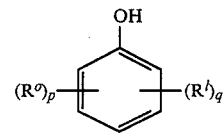  V wherein R$^1$, p and q are as defined in claim 1 and R$^o$ is a residue of formula:

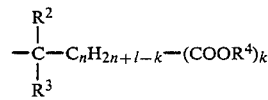  IIa or

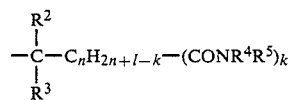  IIb in which R$^2$, R$^3$, R$^4$, R$^5$, n and k are as defined in claim 1.

3. A compound according to claim 2 wherein k is 1.
4. A compound according to claim 3 wherein R$^0$ is a residue of the formula:

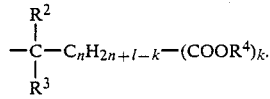

5. A compound according to claim 4 wherein R$^2$ and R$^3$ are each CH$_3$ and R$^1$ is straight or branched chain $C_1$-$C_5$ alkyl.
6. A compound according to claim 2 wherein n is 3.
7. A compound according to claim 1 wherein p is 1.
8. A compound according to claim 7 wherein k is 1.
9. A compound according to claim 8 wherein R$^2$ and R$^3$ are each methyl and R$^1$ is $C_1$-$C_5$ straight or branched chain alkyl.
10. A compound according to claim 1 wherein n is an integer of from 3 to 10.
11. A compound according to claim 2 which does not contain a residue of formula III or IV.
12. A compound according to claim 1 said compound being 2,4-bis(5-methoxycarbonyl-2-methyl-pent-2-yl)phenol.
13. A composition comprising a substrate and, as stabiliser, a compound or a salt thereof as defined in claim 1.
14. A composition according to claim 13 wherein the substrate is an aqueous medium in contact with metals.
15. A composition according to claim 14 wherein the metals are ferrous metals.
16. A composition according to claim 13 wherein the substrate is an organic material susceptible to oxidative decomposition.

* * * * *